(12) United States Patent
Spira et al.

(10) Patent No.: US 9,629,995 B2
(45) Date of Patent: Apr. 25, 2017

(54) BIOMOLECULAR ELECTRONIC DEVICE AND PROCESS OF USE

(75) Inventors: Micha Spira, Jerusalem (IL); Oded Shoseyov, Carmei Yosef (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 567 days.

(21) Appl. No.: 14/122,580

(22) PCT Filed: May 24, 2012

(86) PCT No.: PCT/IL2012/050188
§ 371 (c)(1),
(2), (4) Date: Feb. 28, 2014

(87) PCT Pub. No.: WO2012/160565
PCT Pub. Date: Nov. 29, 2012

(65) Prior Publication Data
US 2014/0171774 A1  Jun. 19, 2014

Related U.S. Application Data

(60) Provisional application No. 61/490,146, filed on May 26, 2011.

(51) Int. Cl.
*A61N 1/05* (2006.01)
*C07K 14/415* (2006.01)
(Continued)

(52) U.S. Cl.
CPC ........ *A61N 1/0543* (2013.01); *A61B 5/04001* (2013.01); *A61N 1/05* (2013.01);
(Continued)

(58) Field of Classification Search
CPC .................................................. G01N 27/327
See application file for complete search history.

(56) References Cited

U.S. PATENT DOCUMENTS 7,253,341 B2 * 8/2007 Wang .................. C07K 14/415
435/252.3
8,957,189 B2 * 2/2015 Wolf .................... B82Y 30/00
436/518
(Continued)

FOREIGN PATENT DOCUMENTS

WO   02/070647 A2   9/2002
WO   2004/022697 A2   3/2004
(Continued)

OTHER PUBLICATIONS

Pfister, et al., "Detection of HSP60 on the membrane surface of stressed human endothelial cells by atomic force and confocal microscopy", J. Cell. Sci., vol. 118, No. 8, pp. 1587-1594, (2005).
(Continued)

*Primary Examiner* — Nashaat Nashed
*Assistant Examiner* — William W Moore
(74) *Attorney, Agent, or Firm* — Vorys, Sater, Seymour & Pease LLP

(57) ABSTRACT

Provided is a biological membrane including at least one ring-like polypeptide, where the at least one of the ring-like polypeptide is not a membrane protein, a surface being associated with at least one ring-like polypeptide capable of integration into a cell membrane, an electrode including said surface and electronically and biomedical devices including the electrodes for recording and stimulating cell activity.

9 Claims, 16 Drawing Sheets

(51) Int. Cl.
  *G01N 27/327* (2006.01)
  *C07K 14/47* (2006.01)
  *G01N 33/483* (2006.01)
  *A61B 5/04* (2006.01)

(52) U.S. Cl.
  CPC ............ *A61N 1/0541* (2013.01); *C07K 14/47* (2013.01); *G01N 27/327* (2013.01); *G01N 33/4836* (2013.01); *Y10T 428/31681* (2015.04)

(56) References Cited

U.S. PATENT DOCUMENTS

| | | | | |
|---|---|---|---|---|
| 9,051,379 | B2* | 6/2015 | Wolf | B82Y 30/00 |
| 2005/0074763 | A1* | 4/2005 | Wang | C07K 14/415 |
| | | | | 435/6.15 |
| 2006/0172298 | A1* | 8/2006 | Wang | C07K 14/415 |
| | | | | 435/6.15 |
| 2009/0253125 | A9* | 10/2009 | Wang | C07K 14/415 |
| | | | | 435/6.15 |
| 2014/0178483 | A1* | 6/2014 | Wolf | B82Y 30/00 |
| | | | | 424/491 |
| 2015/0152311 | A1* | 6/2015 | Wolf | B82Y 30/00 |
| | | | | 252/75 |
| 2015/0273076 | A1* | 10/2015 | Wolf | B82Y 30/00 |
| | | | | 424/400 |
| 2015/0354001 | A1* | 12/2015 | Porath | G01N 33/48721 |
| | | | | 204/543 |

FOREIGN PATENT DOCUMENTS

| | | | |
|---|---|---|---|
| WO | 2004/109282 | A1 | 12/2004 |
| WO | 2007/007325 | A2 | 1/2007 |
| WO | 2008/111047 | A1 | 9/2008 |
| WO | 2011/027342 | A2 | 3/2011 |

OTHER PUBLICATIONS

Triantafilou, et al., "Fluorescence recovery after photobleaching reveals that LPS rapidly transfers from CD14 to hsp70 and hsp90 on the cell membrane", J. Cell. Sci., vol. 114, No. 13, pp. 2535-2545, (2001).

Dgany, et al., "The Structural Basis of the Thermostability of SP1, a Novel Plant (*Populus tremula*) Boiling Stable Protein", The Journal of Biological Chemistry, vol. 279, No. 49, pp. 51516-51523, (2004).

Wang, et al., "Aspen SP1, An Exceptional Thermal, Protease and Detergent-Resistant Self-Assembled Nano-Particle", Biotechnology and Bioengineering, vol. 95, No. 1, pp. 161-168, (2006).

Holmes, et al., "Structure of Thermolysin Refined at 1•6 Å Resolution", J. Mol. Biol., vol. 160, No. 4, pp. 623-639, (1982).

French, et al., "Voltage-Gated Sodium and Calcium Channels in Nerve, Muscle, and Heart", IEEE Transactions on Nanobioscience, vol. 4, No. 1, pp. 58-69, (2005).

International Search Report for International Application No. PCT/IL2012/050188, three pages, mailed Sep. 21, 2012.

Qin, et al., "Electrodeposition of Single-Metal Nanoparticles on Stable Protein 1 Membranes: Application of Plasmonic Sensing by Single Nanoparticles", Angew. Chem. Int. Ed., vol. 50, pp. 1-6, (2011).

Khoutorsky, et al., "Formation of Hydrophilic Nanochannels in the Membrane of Living Cells by the Ringlike Stable Protein-SP1", Nano Letters, pp. A-D, (2011).

Spira, et al., "Use of Aplysia neurons for the study of cellular alterations and the resealing of transected axons in vitro", Journal of Neuroscience Methods, vol. 69, pp. 91-102, (1996).

Ziv, et al., "Induction of Growth Cone Formation by Transient and Localized Increases of Intracellular Proteolytic Activity", The Journal of Cell Biology, vol. 140, No. 1, pp. 223-232, (1998).

Wang, et al., "Crystallization and preliminary X-ray crystallographic analysis of SP1, a novel chaperone-like protein", Acta Cryst: Biological Crystallography, vol. D59, pp. 512-514, (2003).

Medalsy, et al., "SP1 Protein-Based Nanostructures and Arrays", Nano Letters, vol. 8, No. 2, pp. 473-477, (2008).

Malkinson, et al., "Calcium concentration threshold and translocation kinetics of EGFP-DOC2B expressed in cultured Aplysia neurons", Cell Calcium, vol. 39, vol. 85-93, (2006).

Khoutorsky, et al., "Calpain Inhibitors Alter the Excitable Membrane Properties of Cultured Aplysia Neurons", Journal of Neurophysiology, vol. 100, pp. 2784-2793, (2008).

* cited by examiner

```
     ATGGCAACCAGAACTCCAAAGCTTGTGAAGCACACATTGTTGACTCGGTTCAAGGATGAGATCACACGAGAACAGATCGACAACTACATTAATGACTATA
  1  ----+----|----+----|----+----|----+----|----+----|----+----|----+----|----+----|----+----|----+----|  100
     TACCGTTGGTCTTGAGGTTTCGAACACTTCGTGTGTAACAACTGAGCCAAGTTCCTACTCTAGTGTGCTCTTGTCTAGCTGTTGATGTAATTACTGATAT
   > M  A  T  R  T  P  K  L  V  K  H  T  L  L  T  R  F  K  D  E  I  T  R  E  Q  I  D  N  Y  I  N  D  Y  T

CCAATCTGCTCGATCTCATTCCAAGCATGAAGAGTTTCAATTGGGGCACGGATCTCGGGAGCTAAACCGAGGAGCTAAACACTCATGCCTT
 101 ----+----|----+----|----+----|----+----|----+----|----+----|----+----|----+----|----+----|  200
     GGTTAGACGAGCTAGAGTAAGGTTCGTACTTCTCAAAGTTAACCCCGTGCCTAGAGCCCTCGATTGGCTCCTCGATTTGCTCCTCGATTGGAA
   > N  L  D  L  I  P  S  M  K  S  F  N  W  G  T  D  L  G  M  E  S  A  E  L  N  R  G  Y  T  H  A  F

TGAATCTACATTTGAGAGACTCTGGTTTGCAAGAGTACCTCGATTCTGCTGCTCTTGCTGCATTTGCAGAAGGGTTTTTGCCTACTTTGTCACAGCGT
 201 ----+----|----+----|----+----|----+----|----+----|----+----|----+----|----+----|----+----|----+----|  300
     ACTTAGATGTAAACTCTCTGAGACCAAACGTTCTCATGGAGCTAAGACGAGAACGACGTCTTCCCAAAACGGATGAAACAGTGTCGCA
   > E  S  T  F  E  S  K  S  G  L  Q  E  Y  L  D  S  A  A  L  A  A  F  A  E  G  F  L  P  T  L  S  Q  R

CTTGTGATAGACTACTTTCTCTACTAA
 301 ----+----|----+----|-------  327
     GAACACTATCTGATGAAAGAGATGATT
   > L  V  I  D  Y  F  L  Y  *
```

Figure 4

```
atgcaccaccaccaccacgcaaccagaacttccaaacttgtgaag
 M  H  H  H  H  H  H  A  T  R  T  P  K  L  V  K
cacacattgttgactcggttcaaggatgagatcacacgagaacagatcgacaactacatt
 H  T  L  L  T  R  F  K  D  E  I  T  R  E  Q  I  D  N  Y  I
aatgactataccaatctgctcgatctcattccaagcatgaagagtttcaattggggcacg
 N  D  Y  T  N  L  L  D  L  I  P  S  M  K  S  F  N  W  G  T
gatctgggcatggagtctgcggagctaaaccgaggagctaaacactcatgcctttgaatctaca
 D  L  G  M  E  S  A  E  L  N  R  G  Y  T  H  A  F  E  S  T
tttgagagcaagtctggtttgcaagagtacctcgattctgctgctcttgctgcattgca
 F  E  S  K  S  G  L  Q  E  Y  L  D  S  A  A  L  A  A  F  A
Gaaggtttttgcctactttgtcacagcgtcttgtagatagactattttctctactaa
 E  G  F  L  P  T  L  S  Q  R  L  V  I  D  Y  F  L  Y
```

```
  1 ATGAAGCTTGTGAAGCACACATTGTTGACTCGGTTCAAGGATGAGATCACGAGAACAGATCGACAACTACATTAATGACTATACCAATCTGCTCGATC 100
    ----+----|----+----|----+----|----+----|----+----|----+----|----+----|----+----|----+----|----+----|
    TACTTCGAACACTTCGTGTGTAACAACTGAGCCAAGTTCCTACTCTAGTGCTCTTGTCTAGCTGTTGATGTAATTACTGATATGGTTAGACGAGCTAG
  > M  K  L  V  K  H  T  L  L  T  R  F  K  D  E  I  T  R  E  Q  I  D  N  Y  I  N  D  Y  T  N  L  L  D  L

101 TCATTCCAAGCATGAAGAGTTTCAATTGGGCACGGATCTGGGCATGGAGTCTGCGGAGCTAAACCGAGGAGTCTGCCTCCTATGTGAGTACGAGGATACACTCATGCCTTTGAATCTACATTTGA 200
    ----+----|----+----|----+----|----+----|----+----|----+----|----+----|----+----|----+----|----+----|
    AGTAAGGTTCGTACTTCTCAAAGTTAACCCGTGCCTAGACCCGTACCTCAGACGCCTCAGACGGAGGATACACTCATGCGGAAACTTAGATGTAAACT
  > I  P  S  M  K  S  F  N  W  G  T  D  L  G  M  E  S  A  E  L  N  R  G  Y  T  H  A  F  E  S  T  F  E

201 GAGCAAGTCTGGTTTGCAAGAGTCTCGATTCTGCTGCTCGATTCTGCTGCTAAGAACGACGAGAACAGACTAAACGACGACGTAAACGTCTTCCAAAAACGATGAAAACGTGTCGCAGAACACTATCTGATA 300
    ----+----|----+----|----+----|----+----|----+----|----+----|----+----|----+----|----+----|----+----|
    CTCGTTCAGACCAAACGTTCTCATGGAGCTAAGACGACGAGAACGACGATTGCTGCTCTTGTTGCTGCTCATTTGCTGCTCTTTGCACAGCGTCTTGTGAACTATCTGATAG
  > S  K  S  G  L  Q  E  Y  L  D  S  A  A  L  A  A  F  A  E  G  F  L  P  T  L  S  Q  R  L  V  I  D  Y

301 TTTCTCTACTAA ——— 312
    ----+-----
    AAAGAGATGATT
  > F  L  Y
```

Figure 7

```
  1 ATGAAGCTTGTGAAGCACACATTGTTGACTCGGTTCAAGGATGAGATCACGAGAACAGATCGACAACTACATTAATGACTATACCAATCTGCTCGATC 100
    ----+----|----+----|----+----|----+----|----+----|----+----|----+----|----+----|----+----|----+----|
    TACTTCGAACACTTCGTGTGTAACAACTGAGCCAAGTTCCTACTCTAGTGCTCTTGTCTAGCTGTTGATGTAATTACTGATATGGTTAGACGAGCTAG
  > M  K  L  V  K  H  T  L  L  T  R  F  K  D  E  I  T  R  E  Q  I  D  N  Y  I  N  D  Y  T  N  L  L  D  L

101 TCATTCCAAGCTGCAAGAGTTTCAATTGGGCACGGATCTGGGCATGGAGTCTGCCGATCTCGGGAGCTAAACCGAGGATACACTCATGCCTTTGAATCTACATTTGA 200
    ----+----|----+----|----+----|----+----|----+----|----+----|----+----|----+----|----+----|----+----|
    AGTAAGGTTCGACGTTCTCAAAGTTAACCCGTGCCTAGACCCGTACCTCAGACGGCTAGAGCCCTCGATTTGGCTCCTATGTGAGTACGGAAACTTAGTGTAAACT
  > I  P  S  C  K  S  F  N  W  G  T  D  L  G  M  E  S  A  E  L  N  R  G  Y  T  H  A  F  E  S  T  F  E

201 GAGCAAGTCTGGTTTGCAAGAGTCTTCGATTCTGCTCTTGCTGCATTTGCAGAAGGGTTTTTTGCCTACTTTGTCACAGCGTCTTGTGAATGAAACACGAATGAAACCGAAAACGTCTTCCCAAAAACGATGAAAACGTCGCAGAACACTATCTGATA 300
    ----+----|----+----|----+----|----+----|----+----|----+----|----+----|----+----|----+----|----+----|
    CTCGTTCAGACCAAACGTTCTCAAGAAGCTAAGACGAGAACGACGATGATCTCCAAAAAACGGATGAAACGTCTTCGCAGAACAGTGTCGCAGAACACTACTATCGATA
  > S  K  S  G  L  Q  E  Y  L  D  S  A  A  A  L  A  A  F  A  E  G  F  L  P  T  L  S  Q  R  L  V  I  D  Y

301 TTTCTCTACTAA ——— 312
    ----+-----
    AAAGAGATGATT
  > F  L  Y
```

```
  1   ATGAAGCTTGTGAAGCACACATTGTTGACTCGGTTCAAGGATGAGATCACACGAGAACAGATCGACAACTACATTAATGACTATACCAATCTGCTCGATC   100
      ----+----+----+----+----+----+----+----+----+----+----+----+----+----+----+----+----+----+----+----
      TACTTCGAACACTTCGTGTGTAACAACTGAGCCAAGTTCCTACTCTAGTGTGCTCTTGTCTAGCTGTTGATGTAATTACTGATATGGTTAGACGAGCTAG
    > M  K  L  V  K  H  T  L  L  T  R  F  K  D  E  I  T  R  E  Q  I  D  N  Y  I  N  D  Y  T  N  L  L  D  L

101   TCATTCCAAGCATGAAGAGTTTCAATTGGGCACGGATCTGCGAGCTAAACCGAGAGATACACTCATGCCTTTGAATCTACATTGA   200
      ----+----+----+----+----+----+----+----+----+----+----+----+----+----+----+----+----+----+----+----
      AGTAAGGTTCGTACTTCTCAAAGTTAACCCGTGCCTAGACCGCTCAGACGCTCGATTGGCTCCTATGTGAGTGCGAAACTTAGATGTAAACT
    > I  P  S  M  K  S  F  N  W  G  T  D  L  G  M  E  S  A  E  L  N  R  G  Y  T  H  A  F  E  S  T  F  E

201   GAGCAAGTCTGGTTTGCAAGAGTACTGCGATTCTGCTCTTGCTGCATTTGCAGAAGGGTTTTTTGCCTACTTTGTCACAGCGTCTTGTGATAGACTAT   300
      ----+----+----+----+----+----+----+----+----+----+----+----+----+----+----+----+----+----+----+----
      CTCGTTCAGACCAAACGTTCTCATGACGCTAAGACGAGAACGACGTAAACGACTAAACGGATGAAACGTGCGCAGAACACTATCTGATA
    > S  K  S  G  L  Q  E  Y  C  D  S  A  A  L  A  A  F  A  E  G  F  L  P  T  L  S  Q  R  L  V  I  D  Y

301   TTTCTCTACTAA   312
      ----+----+--
      AAAGAGATGATT
    > F  L  Y
```

Figure 8

```
  1   ATGAAGCTTGTGAAGCACACATTGTTGACTCGGTTCAAGGATGAGATCACACGAGAACAGATCGACAACTACATTAATGACTATACCAATCTGCTCGATC   100
      ----+----+----+----+----+----+----+----+----+----+----+----+----+----+----+----+----+----+----+----
      TACTTCGAACACTTCGTGTGTAACAACTGAGCCAAGTTCCTACTCTAGTGTGCTCTTGTCTAGCTGTTGATGTAATTACTGATATGGTTAGACGAGCTAG
    > M  K  L  V  K  H  T  L  L  T  R  F  K  D  E  I  T  R  E  Q  I  D  N  Y  I  N  D  Y  T  N  L  L  D  L

101   TCTGCCCAAGCATGAAGAGTTTCAATTGGGCACGGATCTGGGCATGGAGTCTGCGGAGCTAAACCGAGGATACACTCATGCCTTTGAATCTACATTTGA   200
      ----+----+----+----+----+----+----+----+----+----+----+----+----+----+----+----+----+----+----+----
      AGACGGGTTCGTACTTCTCAAAGTTAACCCGTGCCTAGACCCGTACCTCAGACGCCTCGATTTGGCTCCTATGTGAGTACGGAAACTTAGATGTAAACT
    > C  P  S  M  K  S  F  N  W  G  T  D  L  G  M  E  S  A  E  L  N  R  G  Y  T  H  A  F  E  S  T  F  E

201   GAGCAAGTCTGGTTTGCAAGAGTACTGCGATTCTGCTCTTGCTGCATTTGCAGAAGGGTTTTTGCCTACTTTGTCACAGCGTCTTGTGATAGACTAT   300
      ----+----+----+----+----+----+----+----+----+----+----+----+----+----+----+----+----+----+----+----
      CTCGTTCAGACCAAACGTTCTCATGACGCTAAGACGAGAACGACGTAAACGACTCTTCCCAAAAACGATGAAACAGTGTCGCAGAACAGTCTGATA
    > S  K  S  G  L  Q  E  Y  L  D  S  A  A  L  A  A  F  A  E  G  F  L  P  T  L  S  Q  R  L  V  I  D  Y

301   TTTCTCTACTAA   312
      ----+----+--
      AAAGAGATGATT
    > F  L  Y
```

Figure 9

```
  1   ATGAAGCTTGTGAAGCACACATTGTTGACTCGGTTCAAGGATGAGATCACACGAGAACAGATCGACAACTACATTAATGACTATACCAATCTGCTCGATC     100
      ----+----|----+----|----+----|----+----|----+----|----+----|----+----|----+----|----+----|----+----|
      TACTTCGAACACTTCGTGTGTAACAACTGAGCCAAGTTCCTACTCTAGTCTTGCTCTTGTCTAGCTGTTGATGTAATTACTGATATGGTTAGACGAGCTAG
    > M  K  L  V  K  H  T  L  L  T  R  F  K  D  E  I  T  R  E  Q  I  D  N  Y  I  N  D  Y  T  N  L  L  D  L

101   TCATTCCAAGCATGAAGAGTTTCAATTGGGGCACGGATCTGGGCATGGAGTCTGCGGAGCTAAACCGAGGATACACTCATGCCTTTGAATCTACATTTGA     200
      ----+----|----+----|----+----|----+----|----+----|----+----|----+----|----+----|----+----|----+----|
      AGTAAGGTTCGTACTTCTCAAAGTTAACCCCGTGCCTAGACCCGTACCTCAGATCTGGAGCCTCGATTGGCTCCTATGTGAGTACGGAAACTTAGATGTAAACT
    > I  P  S  M  K  S  F  N  W  G  T  D  L  G  M  E  S  A  E  L  N  R  G  Y  T  H  A  F  E  S  T  F  E

201   GTGCAAGTCTGGTTTGCAAGAGTACCTCGATTCTGCTGCTCTTGCTGCATTTGCAGAAGGGTTTTTGCCTACTTTGTCACAGCGCGTCTTGTGATAGACTAT     300
      ----+----|----+----|----+----|----+----|----+----|----+----|----+----|----+----|----+----|----+----|
      CACGTTCAGACCAAACGTTCTCATGGAGCTAAGACGAGCTAAAGACGACGTAAACGTCTTCCCAAAAACGGATGAAAACAGTGTCGCAACACTATCTGATA
    > C  K  S  G  L  Q  E  Y  L  D  S  A  A  A  L  A  A  F  A  E  G  F  L  P  T  L  S  Q  R  L  V  I  D  Y

301   TTTCTCTACTAA        312
      ----+----|--
      AAAGAGATGATT
    > F  L  Y
```

Figure 10

SEQUENCE LISTING

```
<160> NUMBER OF SEQ ID NOS: 14

<210> SEQ ID NO 1
<211> LENGTH: 108
<212> TYPE: PRT
<213> ORGANISM: Populus tremuloides

<400> SEQUENCE: 1

Met Ala Thr Arg Thr Pro Lys Leu Val Lys His Thr Leu Leu Thr Arg
1               5                   10                  15

Phe Lys Asp Glu Ile Thr Arg Glu Gln Ile Asp Asn Tyr Ile Asn Asp
            20                  25                  30

Tyr Thr Asn Leu Leu Asp Leu Ile Pro Ser Met Lys Ser Phe Asn Trp
        35                  40                  45

Gly Thr Asp Leu Gly Met Glu Ser Ala Glu Leu Asn Arg Gly Tyr Thr
    50                  55                  60

His Ala Phe Glu Ser Thr Phe Glu Ser Lys Ser Gly Leu Gln Glu Tyr
65                  70                  75                  80

Leu Asp Ser Ala Ala Leu Ala Ala Phe Ala Glu Gly Phe Leu Pro Thr
                85                  90                  95

Leu Ser Gln Arg Leu Val Ile Asp Tyr Phe Leu Tyr
            100                 105

<210> SEQ ID NO 2
<211> LENGTH: 114
<212> TYPE: PRT
<213> ORGANISM: Artificial Sequence
<220> FEATURE:
<223> OTHER INFORMATION: Sp1 mutant variant

<400> SEQUENCE: 2

Met His His His His His His Ala Thr Arg Thr Pro Lys Leu Val Lys
1               5                   10                  15

His Thr Leu Leu Thr Arg Phe Lys Asp Glu Ile Thr Arg Glu Gln Ile
            20                  25                  30
```

```
Asp Asn Tyr Ile Asn Asp Tyr Thr Asn Leu Leu Asp Leu Ile Pro Ser
            35                  40                  45

Met Lys Ser Phe Asn Trp Gly Thr Asp Leu Gly Met Glu Ser Ala Glu
 50                  55                  60

Leu Asn Arg Gly Tyr Thr His Ala Phe Glu Ser Thr Phe Glu Ser Lys
 65                  70                  75                  80

Ser Gly Leu Gln Glu Tyr Leu Asp Ser Ala Ala Leu Ala Ala Phe Ala
                85                  90                  95

Glu Gly Phe Leu Pro Thr Leu Ser Gln Arg Leu Val Ile Asp Tyr Phe
            100                 105                 110

Leu Tyr

<210> SEQ ID NO 3
<211> LENGTH: 103
<212> TYPE: PRT
<213> ORGANISM: Artificial Sequence
<220> FEATURE:
<223> OTHER INFORMATION: Sp1 mutant variant

<400> SEQUENCE: 3

Met Lys Leu Val Lys His Thr Leu Leu Thr Arg Phe Lys Asp Glu Ile
 1               5                  10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
            35                  40                  45

Met Glu Ser Ala Glu Leu Asn Arg Gly Tyr Thr His Ala Phe Glu Ser
 50                  55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 4
<211> LENGTH: 103
<212> TYPE: PRT
<213> ORGANISM: Artificial Sequence
<220> FEATURE:
<223> OTHER INFORMATION: Sp1 mutant variant

<400> SEQUENCE: 4

Met Lys Leu Val Lys His Thr Leu Leu Thr Arg Phe Lys Asp Glu Ile
 1               5                  10                  15

Thr Arg Glu Gln Ile Asp Asn Tyr Ile Asn Asp Tyr Thr Asn Leu Leu
            20                  25                  30

Asp Leu Ile Pro Ser Cys Lys Ser Phe Asn Trp Gly Thr Asp Leu Gly
            35                  40                  45

Met Glu Ser Ala Glu Leu Asn Arg Gly Tyr Thr His Ala Phe Glu Ser
 50                  55                  60

Thr Phe Glu Ser Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100
```

<210> SEQ ID NO 5
<211> LENGTH: 103
<212> TYPE: PRT
<213> ORGANISM: Artificial Sequence
<220> FEATURE:
<223> OTHER INFORMATION: Sp1 mutant variant

<400> SEQUENCE: 5

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Cys Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 6
<211> LENGTH: 103
<212> TYPE: PRT
<213> ORGANISM: Artificial Sequence
<220> FEATURE:
<223> OTHER INFORMATION: Sp1 mutant variant

<400> SEQUENCE: 6

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Cys Pro Ser Met Lys Ser Phe Asn Trp Gly Thr Asp Leu Gly
        35                  40                  45

Met Glu Ser Ala Glu Leu Asn Arg Gly Tyr Thr His Ala Phe Glu Ser
    50                  55                  60

Thr Phe Glu Ser Lys Ser Gly Leu Gln Glu Tyr Leu Asp Ser Ala Ala
65                  70                  75                  80

Leu Ala Ala Phe Ala Glu Gly Phe Leu Pro Thr Leu Ser Gln Arg Leu
                85                  90                  95

Val Ile Asp Tyr Phe Leu Tyr
            100

<210> SEQ ID NO 7
<211> LENGTH: 103
<212> TYPE: PRT
<213> ORGANISM: Artificial Sequence
<220> FEATURE:
<223> OTHER INFORMATION: Sp1 mutant variant

<400> SEQUENCE: 7

Met Lys Leu Val Lys His Thr Leu Leu Thr Arg Phe Lys Asp Glu Ile
1               5                   10                  15

Thr Arg Glu Gln Ile Asp Asn Tyr Ile Asn Asp Tyr Thr Asn Leu Leu
            20                  25                  30

Asp Leu Ile Pro Ser Met Lys Ser Phe Asn Trp Gly Thr Asp Leu Gly

```
              35                  40                  45
Met Glu Ser Ala Glu Leu Asn Arg Gly Tyr Thr His Ala Phe Glu Ser
         50                  55                  60

Thr Phe Glu Cys Lys Ser Gly Leu Gln Glu Tyr Leu Asp Ser Ala Ala
 65                  70                  75                  80

Leu Ala Ala Phe Ala Glu Gly Phe Leu Pro Thr Leu Ser Gln Arg Leu
                 85                  90                  95

Val Ile Asp Tyr Phe Leu Tyr
            100

<210> SEQ ID NO 8
<211> LENGTH: 327
<212> TYPE: DNA
<213> ORGANISM: Populus tremuloides

<400> SEQUENCE: 8
atggcaacca gaactccaaa gcttgtgaag cacacattgt tgactcggtt caaggatgag      60
atcacacgag aacagatcga caactacatt aatgactata ccaatctgct cgatctcatt     120
ccaagcatga gagtttcaa ttggggcacg gatctgggca tggagtctgc ggagctaaac      180
cgaggataca ctcatgcctt tgaatctaca tttgagagca gtctggtttt gcaagagtac     240
ctcgattctg ctgctcttgc tgcatttgca gaagggtttt tgcctacttt gtcacagcgt     300
cttgtgatag actactttct ctactaa                                          327

<210> SEQ ID NO 9
<211> LENGTH: 345
<212> TYPE: DNA
<213> ORGANISM: Artificial Sequence
<220> FEATURE:
<223> OTHER INFORMATION: Sp1 mutant variant

<400> SEQUENCE: 9
atgcaccacc accaccacca cgcaaccaga actccaaaac ttgtgaagca cacattgttg      60
actcggttca aggatgagat cacacgagaa cagatcgaca actacattaa tgactatacc     120
aatctgctcg atctcattcc aagcatgaag agtttcaatt ggggcacgga tctgggcatg     180
gagtctgcgg agctaaaccg aggatacact catgcctttg aatctacatt tgagagcaag     240 tctggttttgc aagagtacct cgattctgct gctcttgctg catttgcaga agggttttg      300 cctactttgt cacagcgtct tgtgatagac tattttctct actaa                      345

<210> SEQ ID NO 10
<211> LENGTH: 312
<212> TYPE: DNA
<213> ORGANISM: Artificial Sequence
<220> FEATURE:
<223> OTHER INFORMATION: Sp1 mutant variant

<400> SEQUENCE: 10
atgaagcttg tgaagcacac attgttgact cggttcaagg atgagatcac acgagaacag      60
atcgacaact acattaatga ctataccaat ctgctcgatc tcattccaag catgaagagt     120
ttcaattggg gcacggatct gggcatggag tctgcggagc taaaccgagg atacactcat     180
gcctttgaat ctacatttga gagcaagtct ggtttgcaag agtacctcga ttctgctgct     240
cttgctgcat ttgcagaagg gttttgcct actttgtcac agcgtcttgt gatagactat     300
tttctctact aa                                                         312
```

```
<210> SEQ ID NO 11
<211> LENGTH: 312
<212> TYPE: DNA
<213> ORGANISM: Artificial Sequence
<220> FEATURE:
<223> OTHER INFORMATION: Sp1 mutant variant

<400> SEQUENCE: 11
atgaagcttg tgaagcacac attgttgact cggttcaagg atgagatcac acgagaacag      60
atcgacaact acattaatga ctataccaat ctgctcgatc tcattccaag ctgcaagagt     120
ttcaattggg gcacggatct gggcatggag tctgcggagc taaaccgagg atacactcat     180
gcctttgaat ctacatttga gagcaagtct ggtttgcaag agtacctcga ttctgctgct     240
cttgctgcat ttgcagaagg gttttttgcct actttgtcac agcgtcttgt gatagactat     300
tttctctact aa                                                         312

<210> SEQ ID NO 12
<211> LENGTH: 312
<212> TYPE: DNA
<213> ORGANISM: Artificial Sequence
<220> FEATURE:
<223> OTHER INFORMATION: Sp1 mutant variant

<400> SEQUENCE: 12
atgaagcttg tgaagcacac attgttgact cggttcaagg atgagatcac acgagaacag      60
atcgacaact acattaatga ctataccaat ctgctcgatc tcattccaag catgaagagt     120
ttcaattggg gcacggatct gggcatggag tctgcggagc taaaccgagg atacactcat     180
gcctttgaat ctacatttga gagcaagtct ggtttgcaag agtactgcga ttctgctgct     240
cttgctgcat ttgcagaagg gttttttgcct actttgtcac agcgtcttgt gatagactat     300
tttctctact aa                                                         312

<210> SEQ ID NO 13
<211> LENGTH: 312
<212> TYPE: DNA
<213> ORGANISM: Artificial Sequence
<220> FEATURE:
<223> OTHER INFORMATION: Sp1 mutant variant

<400> SEQUENCE: 13
atgaagcttg tgaagcacac attgttgact cggttcaagg atgagatcac acgagaacag      60
atcgacaact acattaatga ctataccaat ctgctcgatc tctgcccaag catgaagagt     120
ttcaattggg gcacggatct gggcatggag tctgcggagc taaaccgagg atacactcat     180
gcctttgaat ctacatttga gagcaagtct ggtttgcaag agtacctcga ttctgctgct     240
cttgctgcat ttgcagaagg gttttttgcct actttgtcac agcgtcttgt gatagactat     300
tttctctact aa                                                         312

<210> SEQ ID NO 14
<211> LENGTH: 312
<212> TYPE: DNA
<213> ORGANISM: Artificial Sequence
<220> FEATURE:
<223> OTHER INFORMATION: Sp1 mutant variant

<400> SEQUENCE: 14
atgaagcttg tgaagcacac attgttgact cggttcaagg atgagatcac acgagaacag      60
atcgacaact acattaatga ctataccaat ctgctcgatc tcattccaag catgaagagt     120
```

| | | | | |
|---|---|---|---|---|
| ttcaattggg | gcacggatct | gggcatggag | tctgcggagc | taaaccgagg atacactcat | 180 |
| gcctttgaat | ctacatttga | gtgcaagtct | ggtttgcaag | agtacctcga ttctgctgct | 240 |
| cttgctgcat | ttgcagaagg | gtttttgcct | actttgtcac | agcgtcttgt gatagactat | 300 |
| tttctctact | aa | | | | 312 |

BIOMOLECULAR ELECTRONIC DEVICE AND PROCESS OF USE

The Sequence Listing submitted in text format (.txt) filed on Nov. 26, 2013, named "SequenceListing.txt", created on Nov. 25, 2013, 11.1 KB), is incorporated herein by reference.

TECHNOLOGICAL FIELD

This invention generally relates to biomolecular electronics, to an electronic device for communication with living cells and methods of use.

BACKGROUND

One of the major challenges in the use of multi-microelectrode arrays (MEA) in recording (in vitro and in vivo) neuronal network activities is the very low signal to noise ratio. This limits the monitoring to field potentials (~100 μV) generated by action potentials and precludes the detection of sub-threshold synaptic potentials. Consequently, large efforts are devoted to the development of nanotechnologies to better couple excitable cells to electronic devices.

Currently, extracellular MEA is the only available technique for high temporal resolution for multi unit electrical recordings and stimulation. However, although this technique reflects synchronized sub threshold activity generated by ensembles of nearby neurons, it does not provide direct information on synaptic potential.

On the other hand, sharp intracellular microelectrodes and patch-electrodes enable to resolve sub-threshold events with an excellent signal to noise ratio. However, the use of such electrodes is limited to a relatively small number of neurons. In addition, the duration of recordings and stimulation is limited.

International application nos. WO2004/109282 [1] and WO2008/111047 [2] show that, in cultured non-vertebrate organism, *Aplysia*, by using an array of chemically functionalized electrodes, it is possible to obtain intracellular recordings of neuronal action potential and sub-threshold synaptic potentials. The biological processes enabling these recordings are in line with the observations that the electrodes were engulfed by the *Aplysia*'s neurons and a high seal resistance was generated between the neuron and the electrode and finally that unexpected junctions were formed in the neuron-electrode interface supporting a bidirectional electrical coupling. Thus, an increased conductance of the membrane was observed.

REFERENCES

[1] WO2004/109282
[2] WO2008/111047
[3] WO2002/070647
[4] WO2004/022697
[5] WO2007007325
[6] WO2011/027342
[7] Spira, M. E. et al., Use of *Aplysia* neurons for the study of cellular alterations and the resealing of transected axons in vitro. *J. Neurosci Methods* 69, 91-102 (1996).
[8] Ziv, N. E. et al., Induction of growth cone formation by transient and localized increases of intracellular proteolytic activity. *J. Cell Biol.* 140, 223-32 (1998).
[9] Wang, W. et al., Crystallization and preliminary X-ray crystallographic analysis of SP1, a novel chaperone-like protein. *Acta Crystallogr D Biol Crystallogr* 59, 512-4 (2003).
[10] Wang, W. X. et al., Aspen SP1, an exceptional thermal, protease and detergent-resistant self-assembled nano-particle. *Biotechnol. Bioeng.* 95, 161-8 (2006).
[11] Medalsy, I. et al., SP1 protein-based nanostructures and arrays. *Nano Lett.* 8, 473-7 (2008).
[12] Malkinson, G. et al., Calcium concentration threshold and translocation kinetics of EGFP-DOC2B expressed in cultured *Aplysia* neurons. *Cell Calcium* 39, 85-93 (2006).
[13] Khoutorsky, A. et al., Calpain inhibitors alter the excitable membrane properties of cultured *Aplysia* neurons. *J. Neurophysiol* 100, 2784-93 (2008).

GENERAL DESCRIPTION

The present invention is based on findings by the inventors that ring-like non-membrane polypeptides spontaneously partition (integrate, intercalate, embed) into cell membranes. These ring-like polypeptides orient in the membrane such that they form nanopores within the membrane and subsequently modulate the membrane's properties. The degree of partitioning and generation of the nanopores may be controlled by predefining the number of ring-like non-membrane polypeptides to be integrated in the membrane. The nanopores may be made partially or fully closed, for example, by placing in the nanopores "plugs" in the form of nanoparticles, such as gold nanoparticles.

Interestingly, formation of nanopores in the membrane of an electrically active cell or a cell having physiological response to electric stimulation may provide neuroelectronic interface that may assist in intracellular recordings and stimulation of many such individual cells.

Thus, the invention disclosed herein has the advantage of permitting to control and fine-tune the recording and/or stimulation of a desired cell by controlling the extent of nanopore formation.

Specially, the inventors have found that ring-like polypeptides, such as SP1 and derivatives thereof, which are absent from natural animal cell membranes, form nanopores in membranes of living animals cells and increase the membrane conductance. The integration of such a ring-like polypeptide may be substantially irreversible. However, as demonstrated herein, it is possible to reverse the effect induced by such ring-like polypeptides, as SP1 polypeptide, or a derivative thereof such as 6His-SP1, on the membrane conductance, by addition of, e.g., gold nanoparticles (GNP), as explained hereinabove, either prior to or after the partition of the polypeptides into the membrane.

Therefore, in accordance with a first aspect, the present invention provides a biological membrane comprising at least one ring-like polypeptide, wherein the at least one ring-like polypeptide is not a membrane protein (or is not a membrane protein naturally associated with said biological membrane).

The "ring-like polypeptide" is an oligomeric polypeptide (protein) arranged in a circular ring shape (ring-like), namely having a central cavity (as inner pore or inner hole) and having an outer radius defining the outer rim of the ring-like structure and an inner radius defining the radius of the cavity. The polypeptide may comprise several monomeric subunits, being either identical (homo) or different (hetero) from each other, together having a ring-like structure, e.g., complex polypeptides.

The polypeptide may be a native homo-oligomer or hetero-oligomer comprising monomeric subunits arranged, for example, in a concentric arrangement.

As disclosed herein, the ring-like polypeptide partitioned (integrated, intercalated) in the cell membrane, in accordance with the invention, is a "non-membrane polypeptide" naturally not found in animal cell membranes, e.g., in human cell membranes, under physiological conditions (extracellular or intracellular conditions that may occur in nature for that organism or cell system, in contrast to artificial conditions possibly in a laboratory). In other words, the ring-like polypeptide is not naturally located in the plasma membrane or any membrane of a living animal cell.

In some embodiments, the ring-like polypeptide used in accordance with the invention is a heat shock protein (HSP), a functionally related protein involved in the folding and unfolding of other proteins. The expression of HSP is increased when cells are exposed to elevated temperatures and other stress.

According to some embodiments, the ring-like polypeptide is HSP 60, HSP 70, HSP90.

According to some embodiments, the ring-like polypeptide is thermolysin.

In other embodiments, the ring-like polypeptide is a boiling stable polypeptide, having a structural oligomeric stability following treatment at about 95° C., in an aqueous solution, for at least 10 minutes, as determined by a size fractionation assay.

In further embodiments, the ring-like polypeptide is a denaturant-stable polypeptide, having a structural oligomeric stability of an oligomeric protein following treatment in aqueous solution containing 1:2,000 molar ratio (monomer:SDS), as determined by a size fractionation assay.

Still according to some embodiments, the ring-like polypeptide is a stable protein variant.

In some embodiments, the ring-like polypeptide is stable protein 1 (SP1) polypeptide [3-5].

The preparation, structural modification (mutations) and characteristics of SP1 are disclosed in international patent application nos. WO2002/070647 [3], WO2004/022697 [4], WO2007/007325 [5] and WO2011/027342 [6], and corresponding US patent applications, each being incorporated herein by reference.

SP1 is a homo-dodecamer oligomeric protein, with an outer diameter of 11 nm and an inner diameter of 3 nm. SP1 is naturally localized in the cytoplasm of plant cells and is not found in animal, e.g., mammalian (human or non-human) cells.

In some embodiments, the SP1 polypeptide is the wild type polypeptide (disclosed, for example, in [6] as SEQ ID NO: 4) or any derivatives thereof (disclosed, for example, in any of references [3-6], each being incorporated herein by reference). The term "derivatives thereof" is used herein to denote any genetically modified variant of wild type SP1 including fragments thereof, homologous thereof or mutations thereof. Modifications of the SP1 polypeptide may enhance the protein functionality, for example, in interaction with a surface, as disclosed hereinbelow.

As appreciated by those versed in the art, genetic modification of a polypeptide is of common practice and includes mutations in the polynucleotide encoding the respective polypeptide, such that a selective mutation in the nucleotide sequence would result in a desired amino acid mutation. Any mutation of the SP1 polypeptide referred to herein is a mutation based on the wild-type polypeptide. Mutations in the polypeptide may include substitutions (mutations) of at least one amino acid, deletion of at least one amino acid or addition of at least one amino acid. Thus, the polypeptide used in accordance with the present invention may be selected from the wild-type SP1 polypeptide, cysteine mutated/substituted/added SP1 polypeptide, and histidine mutated/substituted/added SP1 polypeptide.

In some embodiments, the SP1 polypeptide is wild-type SP1 polypeptide (SEQ ID NO:1).

In some embodiments, the SP1 polypeptide is a polypeptide encoded by the polynucleotide deposited in NCBI under GenBank: AJ276517.1 (SEQ ID NO:8).

In other embodiments, the SP1 polypeptide comprises additional histidine residues (SEQ ID NO:2) and encoded by the polynucleotide having the sequence SEQ ID NO:9. The 6His-SP1 derivative describes herein corresponds to SEQ ID NO:2.

In further embodiments, the SP1 polypeptide is a homologous variant to wild type SP1. The homologous variant may comprise for example deletion of amino acids in the N-terminal region of the wild type SP1.

In some embodiments, the SP1 polypeptide is a variant polypeptide with a deletion of amino acids in the N-terminal region. This variant SP1 polypeptide having SEQ ID NO:3, being encoded by the polynucleotide having the sequence SEQ ID NO:10.

In some embodiments, the SP1 polypeptide comprises mutations of amino acids to cysteine. Non-limiting examples for such a cysteine-mutated SP1 polypeptides include SEQ ID NO:4 (encoded by the polynucleotide having the sequence SEQ ID NO:11); SEQ ID NO:5 (encoded by the polynucleotide having the sequence SEQ ID NO:12); SEQ ID NO:6 (encoded by the polynucleotide having the sequence SEQ ID NO:13); and SEQ ID NO:7 (encoded by the polynucleotide having the sequence SEQ ID NO:14).

As described throughout, the non-membrane polypeptides spontaneously partition in the plasma membrane of living animal cells and modulate their properties; the biological membrane thus being regarded as a modified membrane. The "biological membrane" in which the polypeptide, e.g., SP1, is integrated, may be any membrane having at least a bilayer of lipid molecules. The biological membrane is, in some embodiments, a natural membrane, such as a cell membrane (plasma membrane) which includes proteins embedded within the lipid bilayer and which separates the interior of cells from the outside environment.

In some embodiments, the cell of which membrane is modified, in accordance with the invention, is an animal cell.

In some embodiments, the cell is from a vertebrate or non-vertebrate organism.

In some embodiments, the cell is a mammalian cell.

In some embodiments, the cell is a human cell or non human cell.

In some embodiments, the cell is selected from a neuron, a muscle cell, a cell of a secreting gland and others.

In some embodiments, the cell is a human cell selected from a neuron, a muscle cell, a cell of a secreting gland and others.

In some embodiments, the biological membrane is not one which does not comprise any characteristics of a plasma membrane (for example lipids and proteins).

In some embodiments, the biological membrane may be an artificial biological membrane model, such as liposomal membrane, composed of a lipid bilayer.

It should be appreciated that upon integration of the polypeptide, e.g., SP1 into the cell membrane, the polypeptide adopts a spatial orientation with respect to the lipid bilayer. Without wishing to be bound by theory, it is believed that the polypeptide is oriented in the membrane such that transfer of materials through the polypeptide inner pore is enabled, thus constituting after intercalation, the nanopores in the cell membrane.

The terms "nanopore" and "nanochannel" denote the pores (holes) in the membrane. In some embodiments, each of the nanopores has, on average, a diameter of up to about 10 nm; in other embodiments, up to about 3 nm; and in further embodiments, up to 2.5 nm.

In some embodiments, the polypeptide nanopore is associated with a metal nanoparticle, said nanoparticle, when present in the nanopore, acting as a plug which closes the nanopore from material transfer therethrough. The "nanoparticle" may be of any metal or an alloy of metals. Non-limiting examples of such metals are gold, platinum, silver, iron, copper, nickel, palladium, iridium, and titanium.

In some embodiments, the size of the nanoparticle is from about 1 nm to about 10 nm; in other embodiments, from about 1 nm to about 5 nm; and in further embodiments, from about 1 nm to about 3 nm.

In some embodiments, the nanoparticle is a gold nanoparticle. In further embodiments, the polypeptide is SP1 [SEQ ID NO:1], SP1 variant [SEQ ID NO:3] or 6His-SP1 [SEQ ID NO:2]. Thus, the invention provides a biological membrane (modified membrane) comprising SP1 [SEQ ID NO:1] or 6His-SP1 polypeptide [SEQ ID NO: 2], wherein the inner pore of said polypeptide being occupied a gold nanoparticle.

In some embodiments, the modified membrane in which the polypeptide, e.g., SP1 or 6His-SP1 is integrated (whether or not the polypeptide is associated with a metal nanoparticle) may be associated with a surface. The surface may have any predefined geometry that may be a stand-alone construct being used to minimize any possible movement of the membrane and may be composed of a metallic material or coated with such a material. The metal may be any metallic element, compound or alloy that is electrically conductive. In some embodiments, the surface is a metallic surface or coated with a metallic layer rendering it conductive.

In some embodiments, the surface is of a material selected from gold, platinum, silver, nickel, palladium and silicon.

The association with the surface may be through one or more linking groups, which act to link the surface with the polypeptide moiety integrated in said membrane and/or with a region of the cell membrane which is not a region defined by the integrated polypeptide.

The association of the surface with the polypeptide residue, or with other regions of the membrane may be via a pendent (native or modified) bifunctional moiety capable of association with the surface (via one functional group of the bifunctional moiety) and with the polypeptide/membrane (via the same or different group of the bifunctional moiety). The surface binding moiety may be selected from a thiol, a carboxylic acid (or a carboxylate), an amine, an amide, an alcohol (or an alkoxy), a siloxy, and others. The polypeptide/membrane binding moiety may be selected from a thiol, a carboxylic acid (or a carboxylate), an amine, an amide, an alcohol (or an alkoxy), and others.

In some embodiments, the bifunctional moiety is selected from homo-bifunctional linkers and hetero-bifunctional linkers.

In some embodiments, the homo-bifunctional linker, having the same type of group at either end, may be selected from, for example, glutaraldehyde, bis(imidoesters) and bis(succinimidylesters) (also known as NHS esters).

In some embodiments, the hetero-bifunctional linkers, having different type of binding groups, may be selected from, for example, [succinimidyl 3-(2-pyridyldithio)propionate] (SPDP), [succinimidyl trans-4-(maleimidylmethyl) cyclohexane-1-carboxylate] (SMCC) and Succinimidyl-4-(p-maleimidophenyl)butyrate (SMPB).

In some embodiments, the surface and polypeptide/membrane binding moieties are bonded to each other through a linking moiety which may be a straight chain or branched chain organic group, such as a C1-C20 alkylene group. In some embodiments, the linking moiety is a C1-C4 alkylene group.

In some embodiments, the association of the surface with the polypeptide/membrane is via one or more (plurality) amino acid groups, non-limitedly selected from glycine, alanine, histidine, cysteine and methionine residues. As indicated herein, the amino acid may be a pendant group on the polypeptide/membrane structure or a moiety (amino acid) of the polypeptide sequence.

In some embodiments, said amino acid is cysteine.

In some embodiments, the association is via a polymer, a peptide, a carbohydrate, a lipid, or a nucleic acid.

The association with the surface may be by a variety of chemical and/or physical interactions, such as covalent bonding, hydrogen bonding, electrostatic interaction, complexation, van der Walls interaction and ionic interaction. In some embodiments, the interaction is covalent bonding.

The surface, with which the modified membrane of the invention is associated, may be a surface region of at least one element of a device, e.g., an electronic or optical device, e.g., for recording or stimulating a tissue.

In some embodiment, the device is an electronic device. In other embodiments, the surface region is an electrode surface region. In further embodiments, the surface is a surface region of a cell-communicating component of an electrode; the component being adapted for sensing and/or stimulating a cell activity.

In some embodiments, the surface may be at least a surface region of an electrode.

Thus, the invention provides an electrode being associated on at least a region of its surface with a biological membrane comprising at least one ring-like polypeptide. In some embodiments, the at least one ring-like polypeptide is not a membrane protein. In other embodiments, the polypeptide is SP1 [SEQ ID NO: 1], a variant of SP1 [SEQ ID NO:3] or cysteine-mutated variants of SP1 having for example [SEQ ID NO:4], [SEQ ID NO:5], [SEQ ID NO:6] or [SEQ ID NO:7]. In further embodiments, the biological membrane is a membrane of a living animal cell.

As used herein, the electrode of the invention is associated with a current source and configured to apply current to a tissue, ex vivo or in vivo.

The electrode may be any one of a gold electrode, a platinum electrode, a carbon electrode, a silver electrode, a nickel electrode, or a palladium electrode.

The electrode may be a regular electrode or a gate electrode. In some embodiments, the gate electrode may be an ion sensitive gate. The ion-sensitive material may be Aluminum Oxide ($Al_2O_3$), Silicon Nitride ($Si_3N_4$), Indium Tin Oxide ($In_2O_3$—$Sn_2O_3$), Silicon Oxide ($SiO_2$) or Tantalum Oxide ($Ta_2O_5$).

In some embodiments, the electrode is an electrode intended to communicate with cells having electric properties, or having physiological responses to electrical stimulation, such as neurons, muscle cells, and cells of secreting glands.

The electrode may be part of an electrode assembly. In some embodiments, said electrode assembly comprises a pair of source-drain electrodes. In other embodiments, said assembly comprises at least a pair of source-drain electrodes and at least one gate electrode.

As appreciated, the invention permits utilization of ring-like polypeptides, such as SP1 or its various derivatives, to electrically and chemically couple sensing pads of electronic devices (transistors gates or passive electrodes) and living cells. This clearly facilitates assembly of neuroelectronic hybrid systems or generate chemical and electrical coupling in vitro or in vivo.

Electrical communication between an electrode according to the present invention and a cell may achieve one or more of:

1. Detection and recording of the presence of current in cells by the electrode or detection of a current change;
2. Detection and recording of changes in potential on plasma membrane of cells or changes in said potential;
3. Providing current to cells; and
4. Applying an electric field to cells.

The cell which membrane is modified by a polypeptide in accordance with the invention may be a cell ex vivo or in vivo. For some applications, particularly such which require stimulation or recording of cells in vivo, the construction of a modified cell membrane onto, e.g., an electrode surface may be achieved by first associating the polypeptide to said surface and subsequently permitting integration of the polypeptide into a cell membrane in vivo.

Thus, according to another aspect, the present invention provides a surface, e.g., an electrode surface, for adherence of cells thereto, at least a region of the surface being in association with at least one (plurality of) ring-like polypeptide capable of (adapted for, for use in, for permitting) integration into a cell membrane (upon contact therewith and under physiological conditions), said ring like polypeptide not being a membrane protein.

Association between the surface region and the polypeptide is as disclosed hereinabove.

As defined above, the surface may have a predefined geometry, optionally comprising at least one curved structure. The curved structure may be an elliptical structure or generally a micronail structure having a micrometer or nanometer scale contact region with the membrane surface. The "micronail", in the context of the present invention, is a micrometer or nanometer scale protrusion from the surface. The surface may comprise one or more such micronail structures, which may be identical to each other in their chemical properties, shape and size or which differ from each other in at least one of chemical properties, shape and size. Each of the micronails acting as individual spaced apart electrodes, distributed to optimize engulfment/wrapping/internalization by a cell membrane.

The interaction between the surface and the cells membrane, i.e., engulfment/wrapping/internalization, may comprise wrapping (engulfment) of the cells membranes around the surface without disturbing the integrity of the membrane. The surface is defined as having cellular-engulfing promoting properties, resulting from the morphology and dimensions of the surface, and/or from the inherent physical and chemical properties of the surface material from which it is formed (such as metal selected from gold, copper, aluminum, platinum, silver, alloys of these metals or combinations thereof) or which is coated with.

The surface may be coated by molecules that recognize plasma membrane components, such molecules may be selected from a protein, a lipid, a polysaccharide, a glycoprotein, and others. Examples of such molecules are ligand of plasma membrane receptors (or receptor binding parts of said ligand), receptors that recognize plasma membrane components; lectins that bind to plasma membrane glycoproteins; antibodies that recognize plasma membrane components (either proteins or non-proteins) or binding fragments of said antibodies; integrins that recognize short linear amino acids present in extracellular proteins, or a combination of two or more of these proteins.

The structure, dimensions and density of the surface can be optimized to maximize the electrical and chemical coupling between the hybrid components, namely the transistor and the living cell.

In accordance with this aspect of the invention, at least a region of the surface, e.g., electrode surface, is wrapped by the cell (via a mechanism know as phagocytosis/pinocytosis or endocytosis) and in view of the integration of the polypeptide into the cells' membrane, the existing membrane nanopores allow part of the surface to pass through the plasma membrane into (or become in contact, or interact with) the cytoplasm and allow the membrane to close around the surface, forming a giga-seal between the plasma membrane and the surface. The passing of the surface inside the cells' cytoplasm allows sensing and recording at least one of electrical and chemical events inside the cells, as well as electrical stimulation from inside the cells.

According to some embodiments, the present invention provides a metallic surface, e.g., an electrode, wherein at least a region of the surface is associated with a membrane integrated with at least one SP1 polypeptide or any derivative thereof.

In accordance with yet another aspect, the present invention provides a device comprising an electrode arrangement having at least one electrode, wherein at least a region of a surface of the electrode being associated with a modified membrane, as described herein.

In accordance with yet a further aspect, there is provided a device for interaction with a cell, the device comprising an electrode which at least a region of its surface being associated with a modified membrane according to the invention, the interaction being via non-membrane ring-like polypeptides present on the cell membrane, said interaction permitting at least one of a chemical and electrical interaction between the electrode surface and the cell cytoplasm.

In accordance with yet a further aspect, there is provided a device for interaction with a cell, the device comprising an electrode which surface being capable of association with a cell cytoplasm, wherein said surface being associated with at least one non-membrane ring-like polypeptide, said polypeptide being capable of undergoing intercalation into a cell membrane for permitting at least one of a chemical and electrical interaction between the electrode surface and the cell cytoplasm.

Electrical communication using such an electrode or an electric device may be carried out for a variety of purposes ranging from basic research to diagnostic means and biomedical devices being used in numerous cells and tissues.

The tissue cells may be any type of cell of interest, especially for electrical recording/stimulating purposes, the cells are typically (but not exclusively) excitable cells such as neurons, muscles endocrine cells and others (of any species).

The increased conductance observed in the membranes comprising the at least one ring like polypeptide may be used in a variety of experimental technologies such as recording of low signal to noise ratio neuronal network activity in cells and hence to obtain a better understanding of the neural network. Further, the device may be used in multielectrode array (MEA).

The device described throughout may be used for diagnostic.

Further, the electronic device according to the present disclosure may be used for the construction of biomedical devices; especially those which need a functional link between nerves or muscles to electric components.

Thus, in accordance with yet another aspect, the present invention provides a biomedical device, said device comprising an electrode which surface being capable of association with a tissue cell cytoplasm, wherein said surface being associated with at least one non-membrane ring-like polypeptide capable of undergoing intercalation into a cell membrane of said tissue, for permitting at least one of a chemical and electrical interaction between the electrode surface and the cell cytoplasm.

In some embodiments, the biomedical device may be prosthesis (also termed prosthetic), namely an artificial device extension that replaces a missing body part by using mechanical devices with human muscle, skeleton or a system to assist or enhance motor control lost by trauma, disease or defect by functionally linking between the cells and the electronic sensing and recording device as described herein.

An electrode or the device according to the invention may be used, for example, to electrically record cell, e.g., neuronal activity (neuronal signals) in a tissue, ex vivo or in vivo e.g., the brain. This recording may be used to restore mobility or assist in controlling devices. Thus, the invention also provides a recording device, said device comprising an electrode which surface being capable of association with neuronal cells, wherein said surface being associated with at least one non-membrane ring-like polypeptide capable of undergoing intercalation into a cell membrane of said neuron, for permitting at least one of a chemical and electrical interaction between the electrode surface and the neuronal cells.

In some embodiments, the device is used for recording neuronal activity (signal) in vivo, e.g., in the brain to improve, increase or induce mobility or neural stimulation of a body part.

In some embodiments, the biomedical device is an implant.

An electrode or the device according to the invention may be used, for example, as a retinal implant (an intraocular prosthetic device), by electrically stimulating retinal cells. In addition, it may be used as a cochlear implant that is an implanted surgical device that provides a sense of sound.

Thus, the invention also provides a retinal implant, said implant comprising a electrode which surface being capable of association with cells of a tissue region of the retina, wherein said surface being associated with at least one non-membrane ring-like polypeptide capable of undergoing intercalation into a cell membrane of said retina, for permitting at least one of a chemical and electrical interaction between the electrode surface and the retina cells.

In some embodiments, the retinal implant is used for stimulating nerve cells in the retina to induce, improve or increase light sensitivity (and subsequently vision).

The invention further provides an ear implant (e.g., cochlear implant), said implant comprising a electrode which surface being capable of association with cells of a tissue region of the ear (e.g., the inner ear), wherein said surface being associated with at least one non-membrane ring-like polypeptide capable of undergoing intercalation into a cell membrane of said ear region, for permitting at least one of a chemical and electrical interaction between the electrode surface and the ear tissue cells.

In some embodiments, the ear implant is used for stimulating nerve cells in the ear tissues to induce, improve or increase sensitivity to sound (and subsequently hearing).

The invention further provides a method for electrically stimulating cells of a tissue region, said method comprising:
    positioning adjacently to a tissue region a device comprising an electrode which surface being capable of association with cells of said tissue region, wherein said surface being associated with at least one non-membrane ring-like polypeptide capable of undergoing intercalation into cell membranes of cells present in said tissue region,
    permitting internalization/engulfing/wrapping of said cell membranes around said electrode surface and intercalation of said at least one non-membrane ring-like polypeptide in said cell membrane; and
    electrically stimulating said cells in said tissue region.

In some embodiments, the stimulation is in vivo.

In some embodiments, said tissue to be stimulated in accordance with the method of the invention, is a tissue of the eye or the ear.

In further embodiments, said cells are selected from a neuron, a muscle cell, a cell of a secreting gland, and others.

The invention further provides a method for electrically recording cells of a tissue region, said method comprising:
    positioning adjacently to a tissue region a device comprising an electrode which surface being capable of association with cells of said tissue region, wherein said surface being associated with at least one non-membrane ring-like polypeptide capable of undergoing intercalation into cell membranes of cells present in said tissue region,
    permitting internalization/engulfing/wrapping of said cell membranes around said electrode surface and intercalation of said at least one non-membrane ring-like polypeptide in said cell membrane; and
    electrically recording activity of said cells in said tissue region.

In some embodiments, the recording is of a tissue activity in vivo.

In some embodiments, said tissue to be recorded in accordance with the method of the invention, is a brain tissue.

In further embodiments, said cells are neuronal cells.

In accordance with another aspect, the present invention provides a process for the preparation of a modified biological membrane, according to the present invention, the process comprising:
    proving a biological membrane in a growth medium;
    adding an amount of a ring-like polypeptide to the growth medium, wherein said polypeptide is not a membrane polypeptide; and
    allowing said polypeptide to integrate into said membrane and forming nanopores in said membrane thereby resulting in a modified biological membrane.

The term "growth medium" denotes a liquid or gel designed to support the growth of biological membranes. In some embodiments, the biological membrane is a cell membrane and thus the term growth medium denotes a culture medium. The growth medium may comprise, for example, source of amino acids, sugars, antibiotics.

In some embodiments, the biological membrane is an artificial membrane, thus the growth medium is regarded as a medium allowing the stability of the artificial membrane within.

In accordance with this aspect, the amount of ring like polypeptide to be added to the growth medium may be determined a priory in order to allow the control on the amount of nanopores formed within the membrane.

BRIEF DESCRIPTION OF THE DRAWINGS

In order to understand the disclosure and to see how it may be carried out in practice, embodiments will now be described, by way of non-limiting example only, with reference to the accompanying drawings, in which:

FIG. 1A shows voltage drop in response to a constant rectangular current pulse injected into the neuron;

FIG. 1B is a graph showing the relations between Rin and the transmembrane potential;

FIG. 1C is a graph showing the effects of wtSP1 on the transmembrane potential and Rin;

FIG. 1D is a graph showing the rate of SP1-induced membrane depolarization, SP1 application is indicated by an arrow;

FIG. 1E is a graph showing the effects of wtSP1 washing on membrane potential, the onset of the wash is indicated by the dashed line.

FIG. 2A is a graph showing the effect of 6His-SP1 on the transmembrane potential and Rin;

FIG. 2B is a graph showing the dynamics of 6His-SP1-induced membrane depolarization;

FIG. 2C is a graph showing the membrane potential and input resistance of a single neuron before and after the application of 2 μM 6His-SP1-GNP complex;

FIG. 2D is a graph showing the resting potential after the application of 6His-SP1-GNP complex;

FIGS. 2E and 2F are graphs showing effect of application of GNPs to the bathing solution after the onset of 6His-SP1-induced effects on the transmembrane potential and Rin (FIG. 2E) and membrane depolarization (FIG. 2F);

FIGS. 2G and 2H are graphs showing the effects of application of GNPs to the bathing solution after the onset of wtSP1-induced effects on the transmembrane potential and Rin (FIG. 2G) and membrane depolarization (FIG. 2H).

FIG. 4 depicts the SP1 nucleotide sequence (SEQ ID NO:8) and the deduced (encoded) SP1 protein sequence (SEQ ID NO:1).

FIG. 5 depicts a nucleotide sequence (SEQ ID NO:9) and the deduced SP1 variant (mutant) protein sequence (SEQ ID NO:2).

FIG. 6 depicts a nucleotide sequence (SEQ ID NO:10) and the deduced SP1 variant (mutant) protein sequence (SEQ ID NO:3).

FIG. 7 depicts a nucleotide sequence (SEQ ID NO:11) and the deduced SP1 variant (mutant) protein sequence (SEQ ID NO:4).

FIG. 8 depicts a nucleotide sequence (SEQ ID NO:12) and the deduced SP1 variant (mutant) protein sequence (SEQ ID NO:5).

FIG. 9 depicts a nucleotide sequence (SEQ ID NO:13) and the deduced SP1 variant (mutant) protein sequence (SEQ ID NO:6).

FIG. 10 depicts a nucleotide sequence (SEQ ID NO:14) and the deduced SP1 variant (mutant) protein sequence (SEQ ID NO:7).

DETAILED DESCRIPTION OF EMBODIMENTS

Materials and Methods

Neurons Culture

Figure 1A:
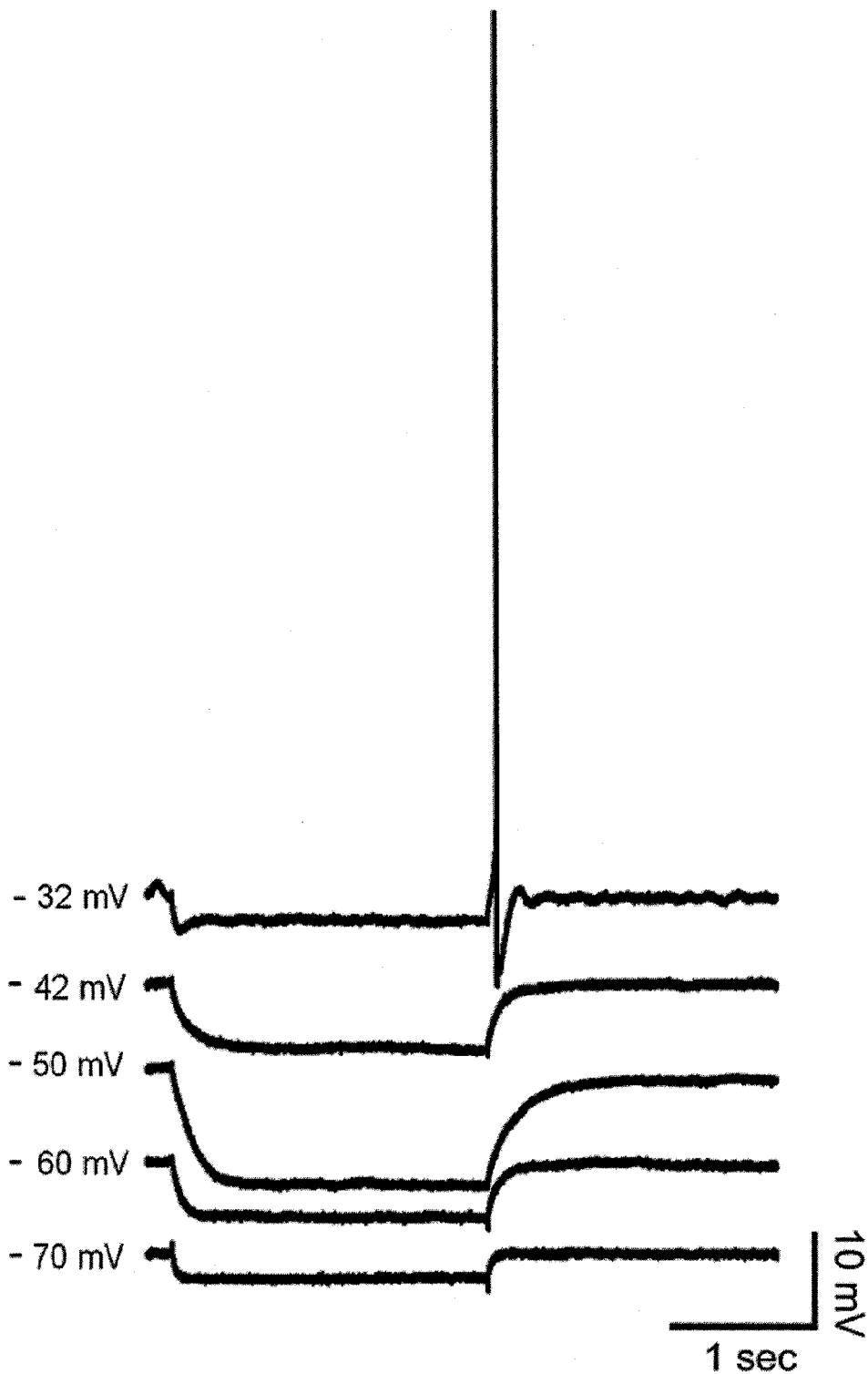
FIGS. 1A-1E are graphs showing that wtSP1 induces membrane depolarization and decreased input resistance.

Left upper quadrant neurons (LUQ) from the abdominal ganglion of juvenile *Aplysia* (2-5 g) were cultured, as previously described [7, 8].

Briefly, animals were anesthetized by injection of isotonic $MgCl_2$ solution. The ganglia were isolated and incubated for 1.5-3 h in 1% protease (Type IX, Sigma) at 34° C. The ganglia were then de-sheathed, and the cell bodies or their neurons with their long axons were pulled out with sharp micropipets and placed on poly-L-lysine coated (Sigma) glass bottom culture dishes. The culture medium consisted of 10% filtered hemolymph from *Aplysia faciata* collected along the Mediterranean coast, and L-15 (Gibco-BRL) supplemented for marine species. Twenty-four hours after plating dishes were transferred to an 18° C. incubator. Experiments were preformed 3-5 days after plating.

Electrophysiology

All experiments were performed at room temperature in artificial sea water (ASW) composed of NaCl 460 mM, KCL 10 mM, $CaCl_2$ 10 mM, $MgCl_2$ 55 mM and HEPES [N-(2-hydroxyethyl)-piperazine-N'-2-ethanesulfonic acid, Sigma] 11 mM, adjusted at pH 7.6.

Recording and stimulation of LUQ neurons were conducted in current-clamp mode using sharp 5-10 MΩ glass microelectrodes filled with 2M KCl. The microelectrode served for both current injection and voltage recording (Axoclamp-2A; Axon Instruments). Signals were digitally recorded by means of a Digidata 1322A interface (Axon Instruments, Union City, Calif.) and analyzed with Clampfit software (Axon Instruments).

SP1 and 6His-SP1

Expression and purification of all SP1 mutants were performed as described previously, wild-type SP1 (wtSP1) [9, 10] and 6His-SP1 [11]. SP1 and 6His-SP1 were applied to the bathing solution in ASW to generate a final concentration of 2 μM.

Ca Imaging

Calcium imaging was conducted as previously reported [12]. Briefly, the system used for confocal calcium imaging consisted of an Olympus microscope IX70 and a Bio-Rad (Hercules, Calif.) Radiance 2000/AGR-3 confocal imaging system. The objective used was an Olympus planApo 60×1.4 NA oil objective. The images were collected and processed using LaserSharp and LaserPix BioRad software, respectively. For the experiments, fluo-4 10 mM (pentapotassium salt, Invitrogen) in 0.5 KCl was pressure microinjected into the neurons. Imaging was preformed after the dye has equilibrated throughout the main axon and the small neuritis (approximately 30 minutes after the injection). Fluo-4 was excited with 488 nm (Argon laser), and the emission was collected at 500-560 nm.

EXAMPLE 1

Partition of wtSP1 into Plasma Membrane

The purpose of this experiment was to examine if wtSP1, dispersed in a physiological solution, spontaneously partition into the bi-lipid membrane of living neurons and form nanopores.

Methods

The culture medium, which contains *Aplysia* hemolymph, was replaced by artificial sea water (ASW), an ionic solution. A cultured neuron was then impaled by a sharp glass microelectrode that served for both current injections and voltage recordings [13].

Results

The input resistance (Rin) of the neuron was calculated from the transmembrane voltage drop generated by small intracellular hyperpolarizing rectangular 0.3 nA current pulses lasting 2 s (FIG. 1).

The relations between the transmembrane potential and the neuron's input resistance were determined in control experiments by intracellular injection of the hyperpolarizing rectangular current pulses while shifting the membrane potential with a DC current source from −70 to −30 mV.

FIG. 1A corresponds to data from a control neuron showing the relationships between the input resistance and transmembrane potential which was established by measuring the voltage drop in response to a constant rectangular current pulse injected into the neuron, while shifting the transmembrane voltage to various values by DC current. The value to which the membrane potential was set is indicated on the left-hand side.

Figure 1B:
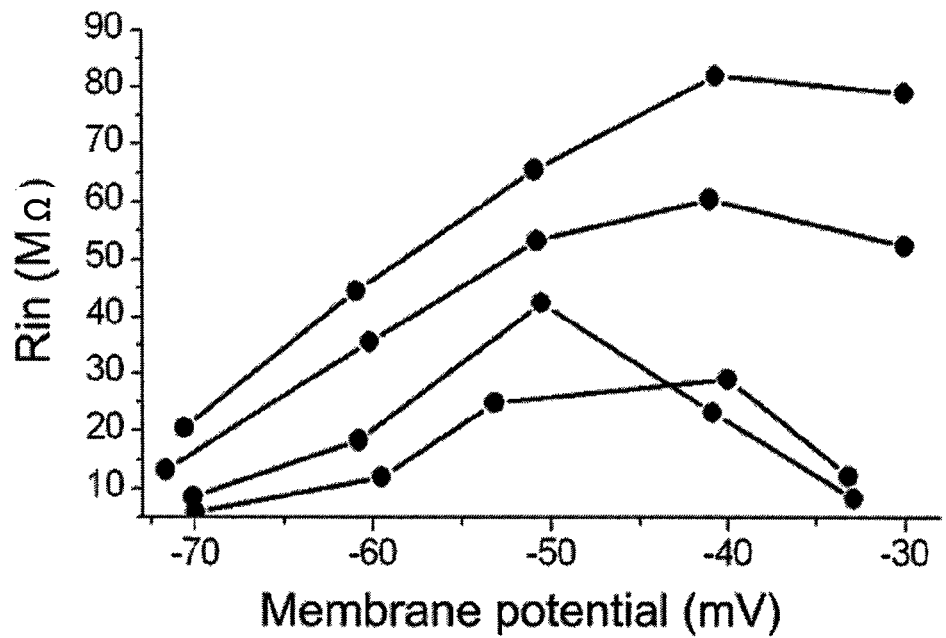

The relation between Rin and the transmembrane potential in four control neurons is shown in FIG. 1B. Rin was calculated from the voltage drop generated by a 2 sec long, 0.3 nA hyperpolarizing square pulls current injection.

These experiments revealed that the Rin of cultured LUQ neurons is nonlinearly related to the membrane potential, reaching a maximum at about −50 mV. Depolarizing the membrane potential to approximately −30 mV lead to increased membrane conductance and often generated an action potential (FIG. 1A).

Figure 1C:
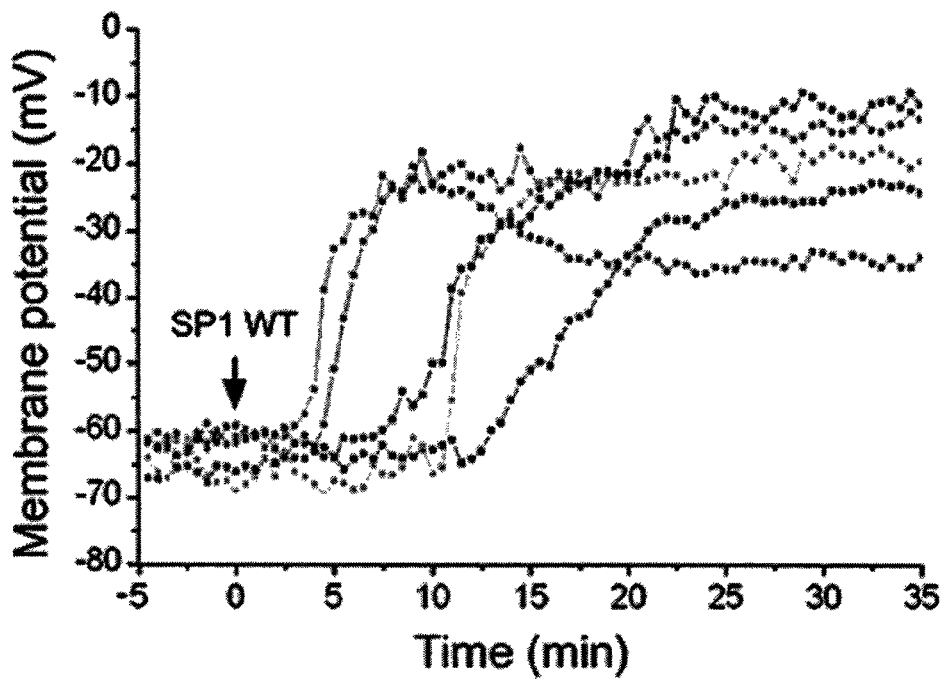
Figure 1D:
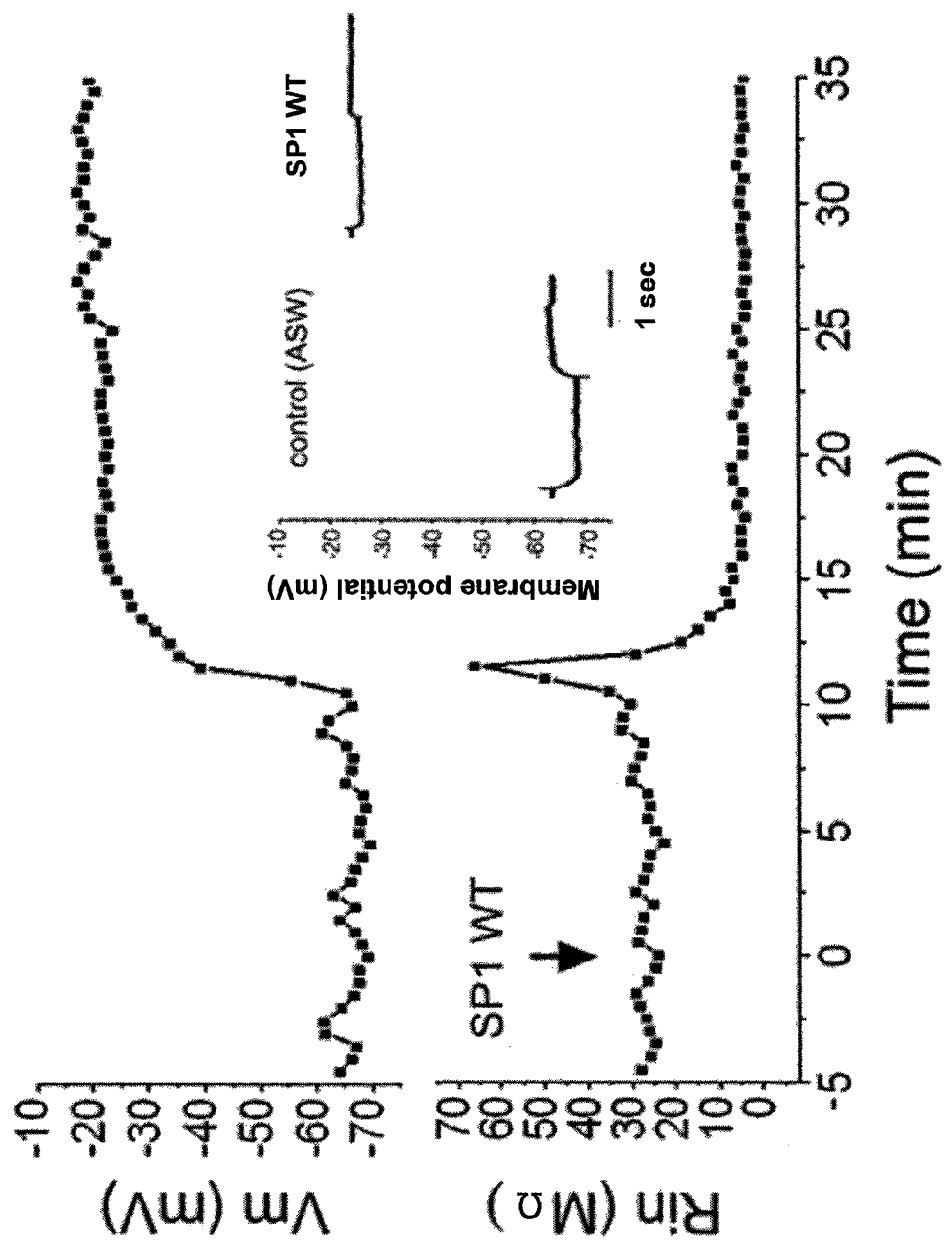

With this background information at hand, and in order to evaluate directly the effects of wtSP1 on the transmembrane potential and Rin, wtSP1 (2 μM) was applied to the bathing solution while the membrane potential and input resistance were measured (arrow, FIG. 1C). Bath application of wtSP1 induced membrane depolarization associated with changes in Rin (FIGS. 1C and 1D). FIG. 1D shows the variability in the rate of SP1-induced membrane depolarization (n=5).

Within variable time of 3-25 min. of wtSP1 application, the membrane potential (which was set initially to −60 mV by DC current injection) depolarized, reaching a value of −20±3.8 mV (n=5), within approximately 20 min (FIG. 1C). The averaged depolarization rate was 5.03±1.03 mV/min (n=5). In parallel to the depolarization, the input resistance initially increased and then rapidly decreased (FIG. 1C, low panel). Note that approximately 10 min. after SP1 application the membrane depolarized and the input resistance was transiently elevated. Insert in FIG. 1C—representative traces of the recorded voltage drop in response to a constant rectangular current injection pulse before and 15 minutes after wtSP1 application.

The initial increase in Rin reflects depolarization-induced inactivation of ion channels, as revealed in the control experiments (FIGS. 1A and 1B). Yet, in contrast to the control experiments, after the initial increase in Rin the input resistance of the neurons sharply dropped to values lower than the control that is prior to application of wtSP. In 4 out of 5 experiments the initial increase in Rin was followed by the decrease of Rin to 28±11% of the value prior to wtSP1 application (from 16.6±3.2 MΩ to 4.51±1.91 MΩ, respectively).

Figure 1E:
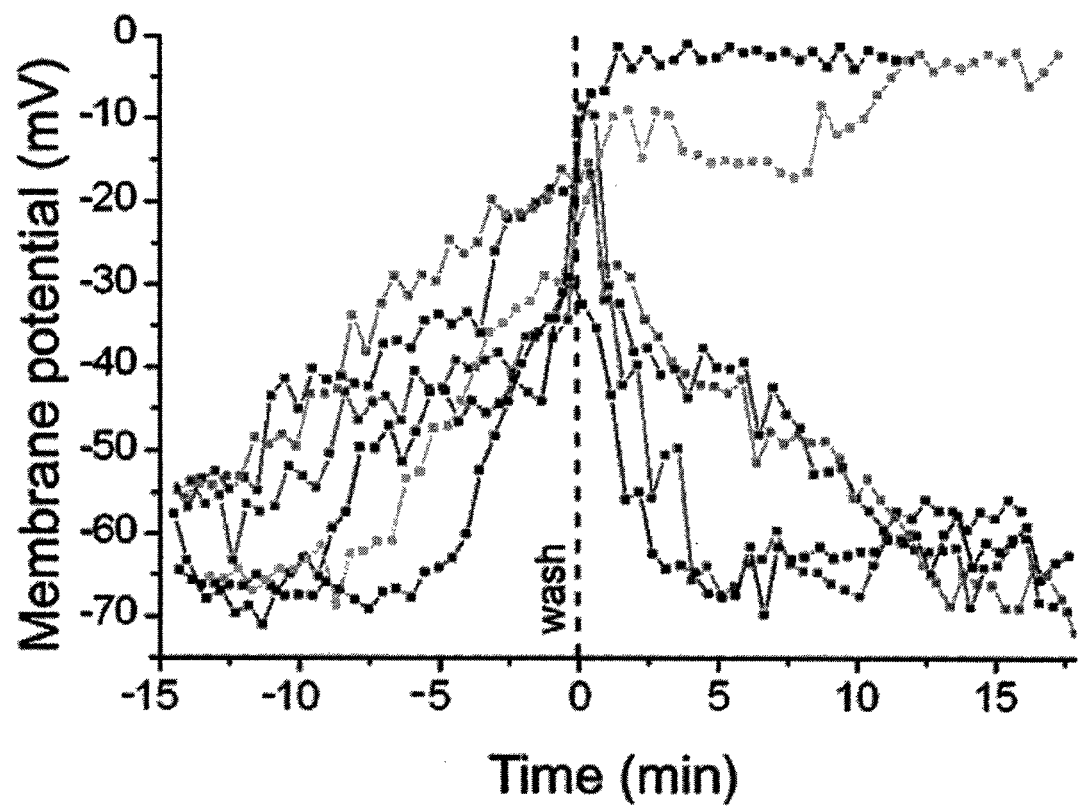

The documented reduction in Rin represents the partitioning of wtSP1 to the plasma membrane and suggests that the ring-like protein serves as an open nanochannel when in contact with the plasma membrane. wtSP1 can be removed from the plasma membrane by washing with ASW (FIG. 1E). In four out of the six experiments, the washout of wtSP1 was associated with recovery of the membrane potential and Rin within 3-12 minutes (FIG. 1E).

In two out of the 6 experiments, removing wtSP1 did not lead to recovery of the membrane potential and Rin. These neurons eventually degenerated. This variability most likely reflect differences in the level of wtSP1-induced increase in the free intracellular calcium concentration ($[Ca^{2+}]_i$). Imaging of the $[Ca^{2+}]_i$ by fluo-4 revealed that wtSP1 application leads to gradual elevation of the $[Ca^{2+}]_i$ (data not shown).

Without wishing to be bound by theory, membrane depolarization and decreased Rin by wtSP1 could be generated by two mechanisms: (a) the wtSP1 allows ion flow through its 3 nm inner pore or alternatively (b) the incorporation of wtSP1 into the membrane distorts the organization of the bi-lipid membrane leading to ion leakage. Both mechanisms could lead to membrane depolarization and increased conductance.

EXAMPLE 2

Partition of 6His-SP1 into Plasma Membrane

The purpose of this experiment was to evaluate whether the wtSP1-induced reduction in Rin was mediated by ion flow through the inner nanopore or in a different way. Therefore, the response of the neurons to the application of a modified derivative of wtSP1, the 6His-SP1 [11] was tested.

Results

Initially, the effects of 6His-SP1 application on the resting potential and input resistance were evaluated using the approach described above.

Figure 2A:
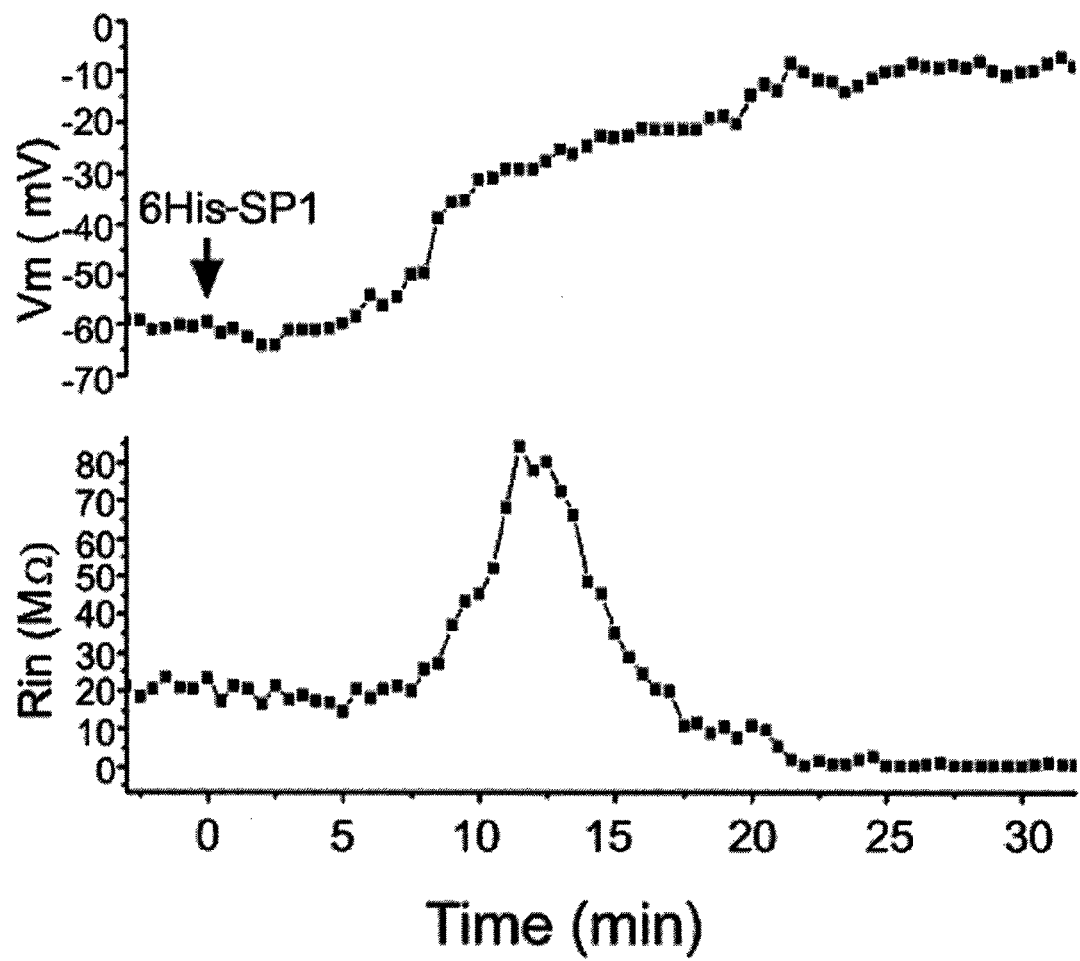
FIGS. 2A-2H are graphs showing the reversible conductance blockade of the 6HIS-SP1 inner pore by gold nanoparticles.

FIG. 2A shows that application of 2 μM 6His-SP1 resulted in membrane depolarization initially associated with a transient increase in the input resistance followed by a drop of the input resistance to below the control level. Similarly to wtSP1, 2 μM 6His-Sp1 induced membrane depolarization to a mean value of −19.4±5.7 mV within ~30 min. following application (n=5, FIG. 2A). This was associated with a decreased Rin to an average value of 21±12% of the value before application (from a mean of 27.34±5.12 MΩ to 6.3±2.51 MΩ, n=6, FIG. 2A low panel, representative alteration). The onset and rate of 6His-SP1-induced membrane depolarization was somewhat slower than that of the wtSP1 (onset time of 11.78±2.63 min. and 7.34±1.73 min. respectively and depolarization rate of 2.15±0.15 mV/min and 5.03±1.03 mV/min respectively, n=5).

Figure 2B:
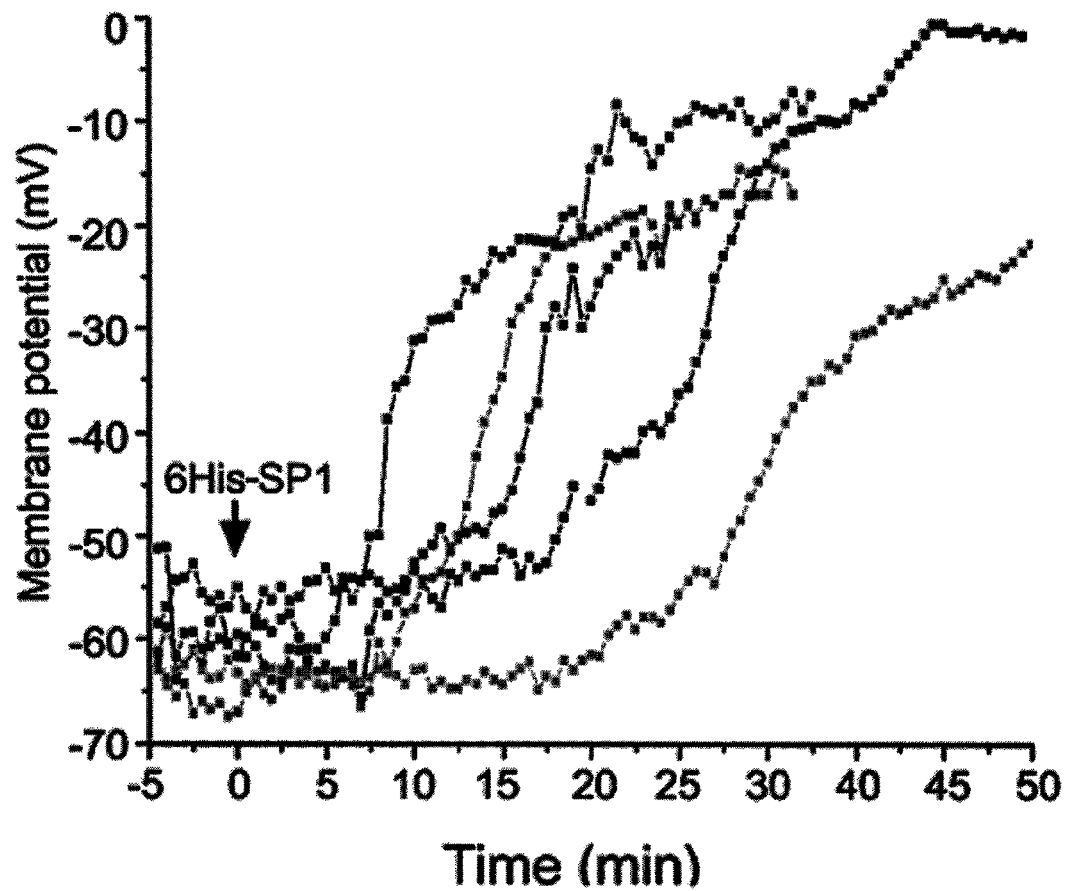

It was thus concluded that 6His-SP1 partition into the plasma membrane was as for wtSP1. FIG. 2B shows that the dynamics of 6His-SP1-induced membrane depolarization was similar to that of wtSP1. When the inner pore of the 6His-SP1 was blocked by GNPs prior to its bath application, the membrane potential and Rin were not altered.

Figure 2C:
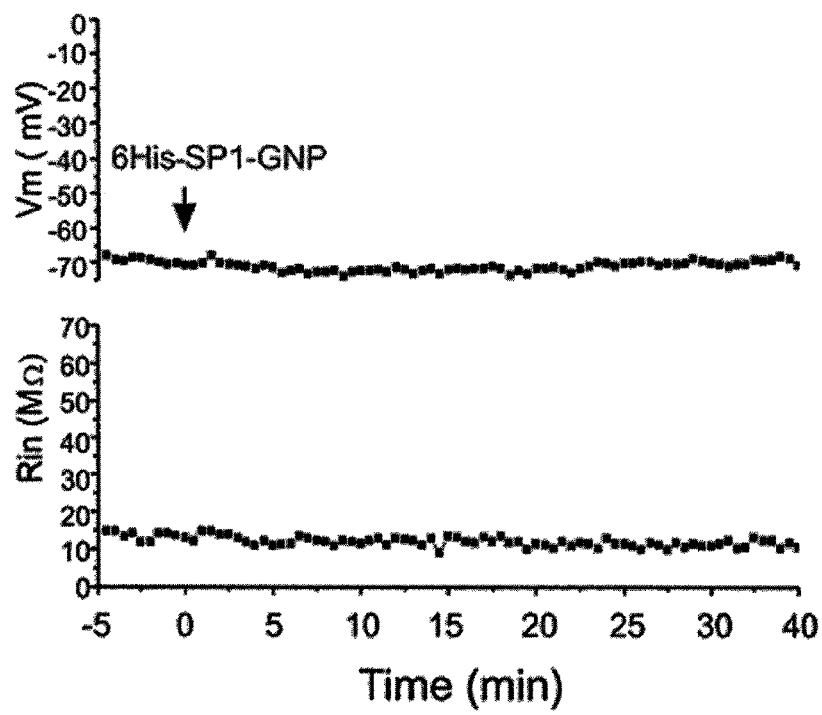
Figure 2D:
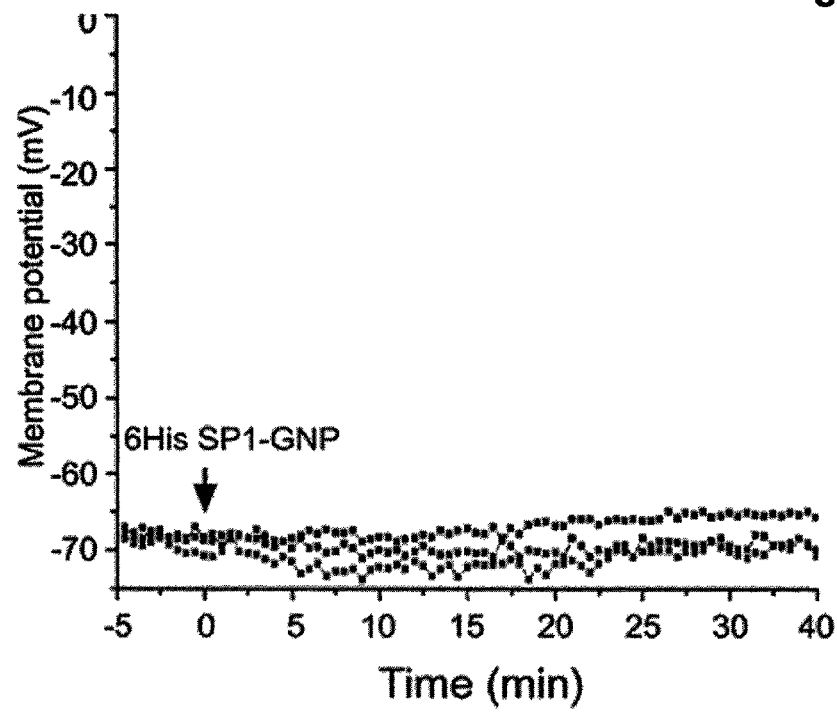

FIG. 2C shows measurements of the membrane potential and input resistance of a single neuron before and after the application of 2 μM 6His-SP1-GNP complex. FIG. 2D shows that the resting potential (3 cells) was not altered by the application of 2 μM 6His-SP1-GNP complex. Bath application of 6His-SP1, to which a GNP (6His-SP1-GNP) were attached prior to its application, did not affect the transmembrane potential or the Rin (FIGS. 2C and D, n=3).

Without wishing to be bound by theory, this result suggests that the inner pore of the SP1 complex underlies the increased membrane conductance. Hypothetically, it is conceivable that binding of GNP to 6His-SP1 prior to its bath application would interfere with the partitioning of the 6His-SP1-GNP into the membrane, thus, preventing its effect on the conductance of the membrane.

Figure 2E:
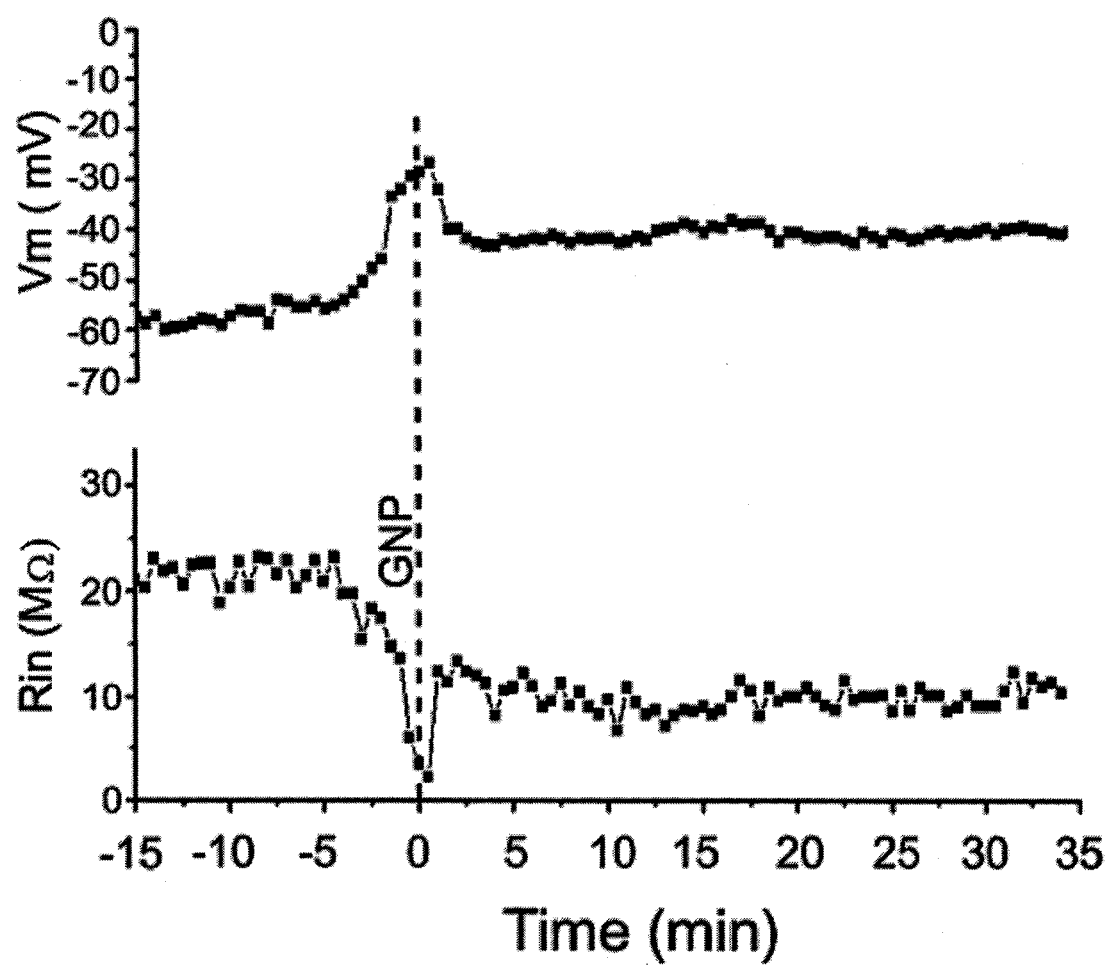
Figure 2F:
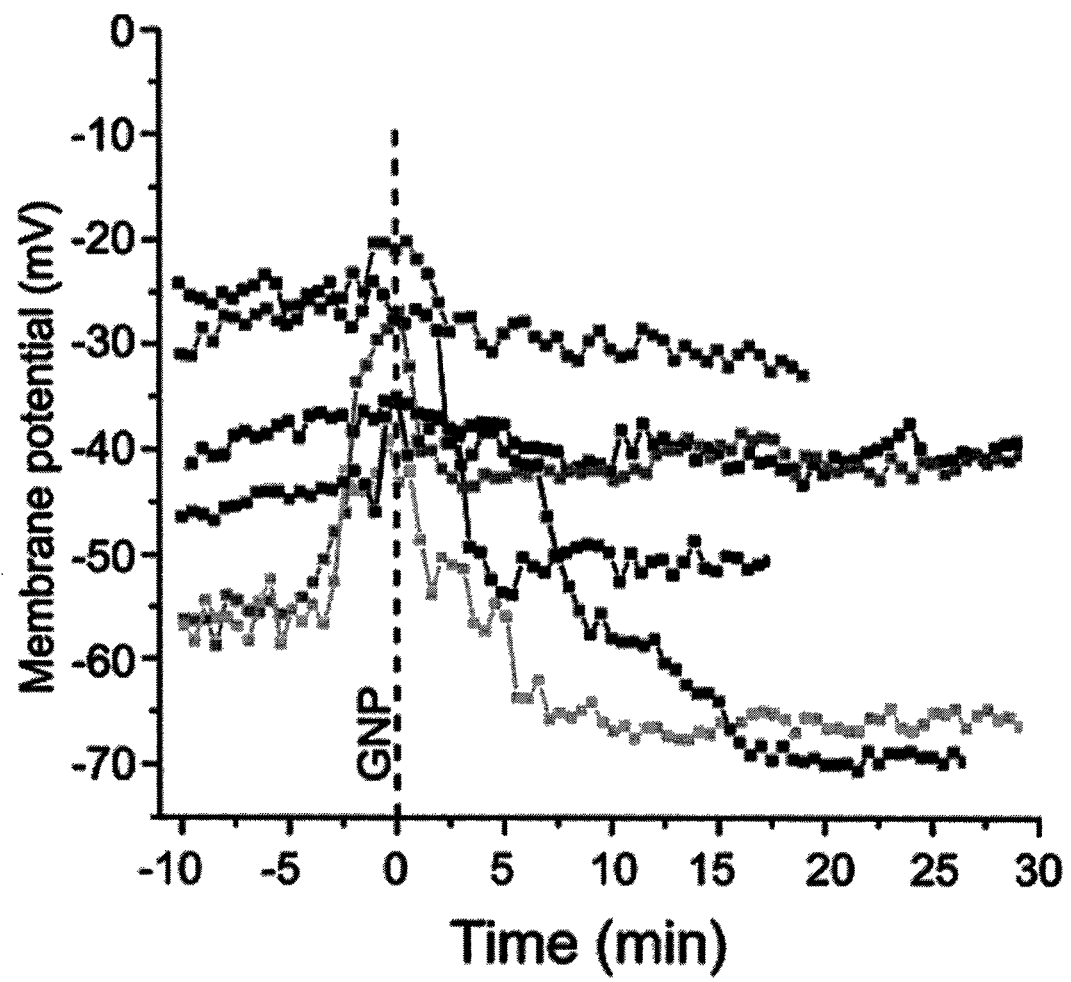
Figure 2G:
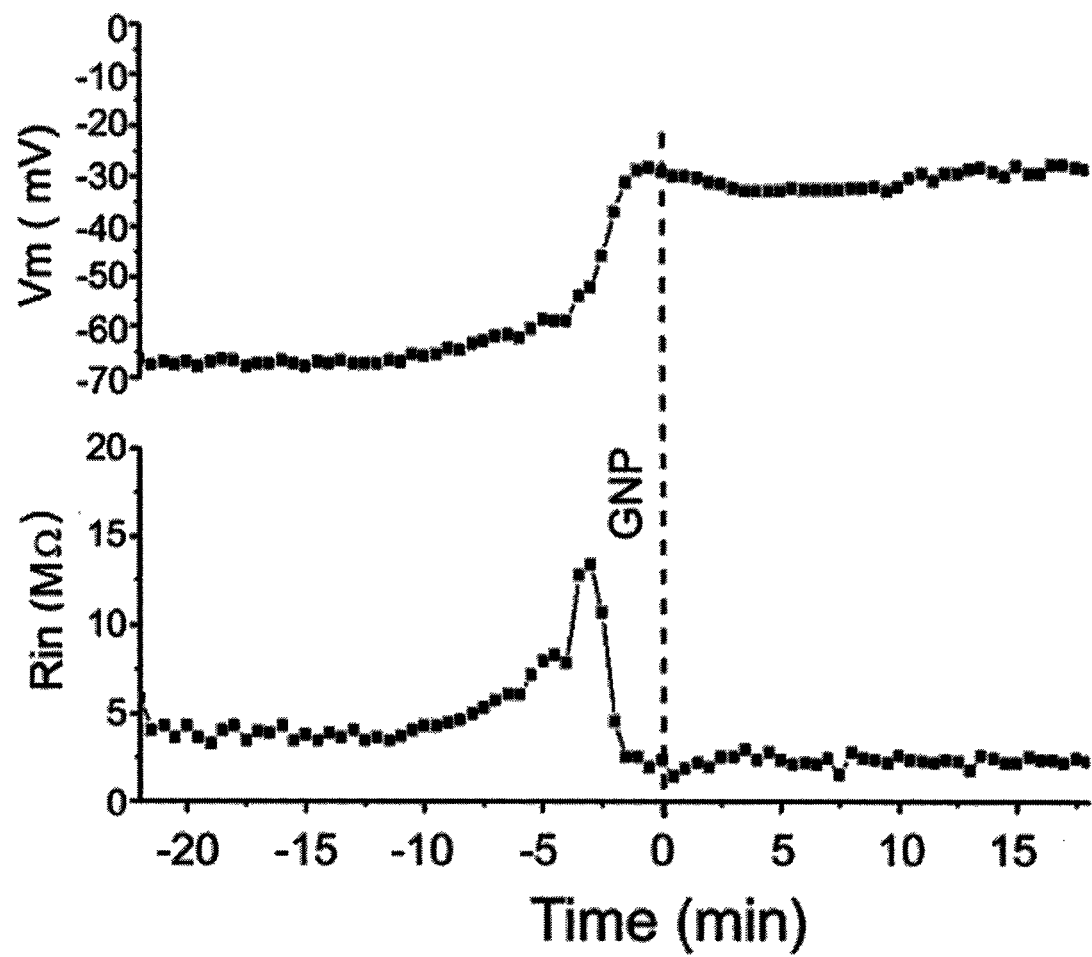
Figure 2H:
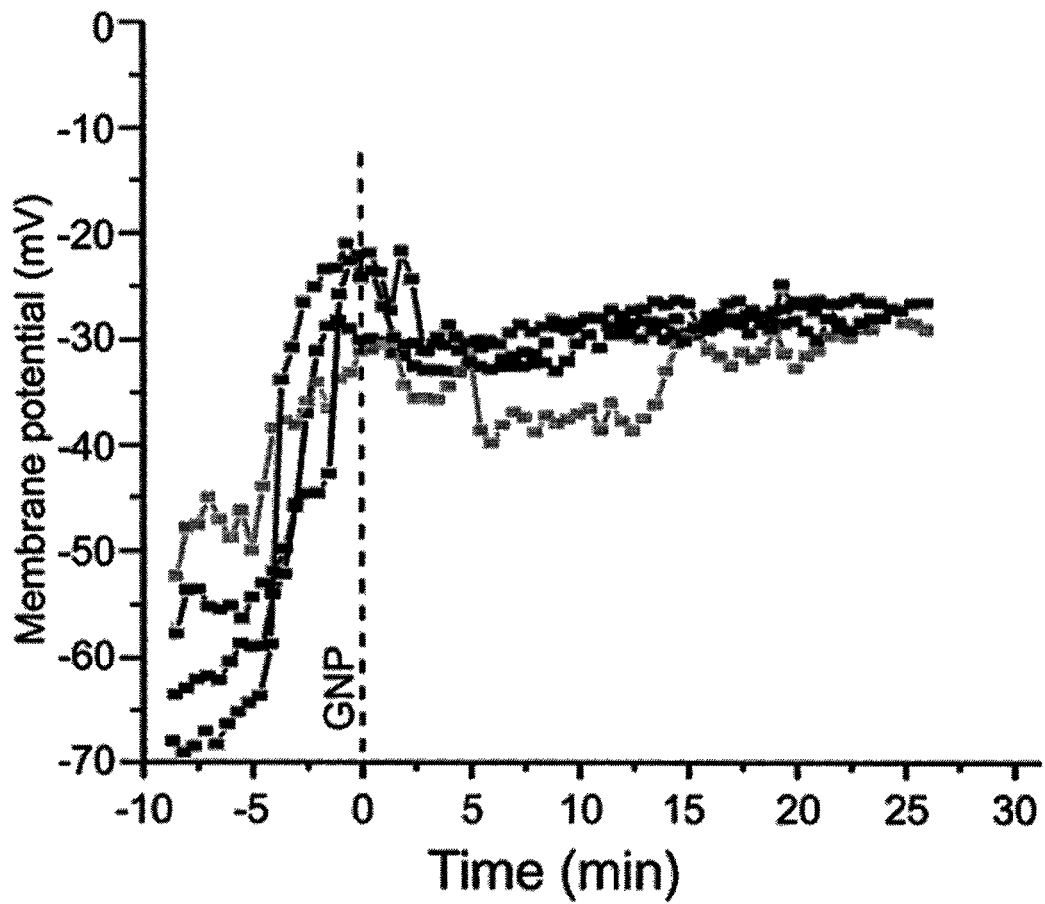
Figure 3:
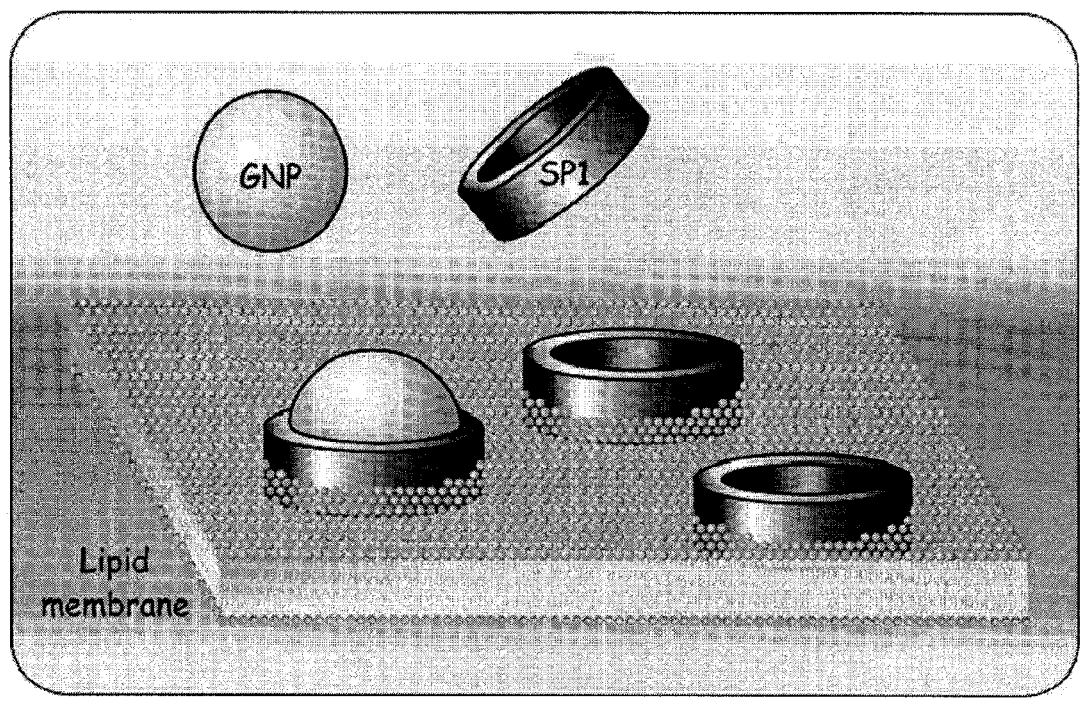
FIG. 3 is a schematic representation showing the attachment of an SP1 derivative to the plasma membrane and the blocking of the SP1 conducting pore by a nano-gold particle.

To differentiate between these possibilities 2 μM 6His-SP1 was applied, and shortly after the onset of membrane depolarization, 4 μM GNPs was applied to the bathing solution (FIGS. 2E and 2F, n=6). Application of GNPs (4 μM) to the bathing solution after the onset of 6His-SP1-induced depolarization, resulting in partial recovery of the input resistance and the transmembrane voltage, FIGS. 2E and 2F.

In all experiments it was found that the addition of GNPs reversed the initial effects of 6His-SP1 on the membrane potential and Rin. The effectiveness of GNPs application revealed large variability ranging from mild improvement to complete recovery. On average, following the application of the GNPs the membrane potential was hyperpolarized by 17.33±3.19 mV (n=6) within 10 minutes of GNPs application, whereas Rin recovered by GNP application to 91±14% of the initial value.

These results are consistent with the hypothesis that the GNP binds to 6His-SP1 that was incorporated into the plasma membrane and reduces the 6His-SP1 pore conductance.

To address potential nonspecific effects of the GNPs on the membrane ion conductance, GNPs were applied to neurons pre-incubated with wtSP1 (FIGS. 2G and H). The effects of GNPs on the resting potential and input resistances are expressed only when 6His-SP1 is incorporated into the plasma membrane. Thus, when wtSP1 is applied to the bathing solution and exerts its effects, application of 4 μM GNPs is ineffective in terms of reversing the effects of SP1 on membrane potential and the input resistance (FIGS. 2H and 2G).

Under these conditions, GNPs application led to 4±1.08 mV membrane hyperpolaryzation (n=4), a significantly smaller hyperpolaryzation than that produced by application of GNPs to 6His-SP1 treated neurons ($p<0.05$, independent samples t-test). Rin did not recover following GNPs application to a wtSP1 treated neuron (remained at 33±10% relative to the initial values, n=4).

Without wishing to be bound by theory, these results indicate that the recovery of the membrane potential and Rin by the GNPs following 6His-SP1 application is the outcome of specific clogging of the 6His-SP1 inner pore by the applied GNPs (FIG. 3).

The invention claimed is:

1. A eukaryotic cell membrane comprising at least one stable protein 1 (SP1) ring-like polypeptide, wherein the at least one ring-like polypeptide is not a membrane protein and has an amino acid sequence selected from the group consisting of the wild type SP1 polypeptide amino acid sequence of SEQ ID NO:1, a polypeptide having the amino acid sequence of SEQ ID NO:2, a polypeptide having the amino acid sequence of SEQ ID NO:3, a polypeptide having the amino acid sequence of SEQ ID NO:4, a polypeptide having the amino acid sequence of SEQ ID NO:5, a polypeptide having the amino acid sequence of SEQ ID NO:6, and a polypeptide having the amino acid sequence of SEQ ID NO:7.

2. The membrane according to claim 1, wherein the cell is a neuronal cell, a muscle cell, or a cell of a secreting gland.

3. The membrane according to claim 1, wherein the SP1 polypeptide is a wild type SP1 polypeptide having the amino acid sequence of SEQ ID NO:1, or a polypeptide having the amino acid sequence of SEQ ID NO:3.

4. The membrane according to claim 1, wherein the SP1 polypeptide has the amino acid sequence of SEQ ID NO:2, the amino acid sequence of SEQ ID NO:4, the amino acid sequence of SEQ ID NO:5, the amino acid sequence of SEQ ID NO:6, or the amino acid sequence of SEQ ID NO:7.

5. The membrane according to claim 1, wherein the at least one SP1 ring-like polypeptide has an inner nanopore.

6. The membrane according to claim 1, wherein the membrane is associated with a surface.

7. The membrane according to claim 6, wherein the surface is at least a surface region of an electrode.

8. The membrane according to claim 7, wherein the electrode is at least a region of an electronic device.

9. The membrane according to claim 5 wherein a metal nanoparticle is associated with the inner nanopore.

* * * * *